US009408879B2

(12) United States Patent
Guglielmetti et al.

(10) Patent No.: US 9,408,879 B2
(45) Date of Patent: Aug. 9, 2016

(54) BIFIDOBACTERIUM BIFIDUM STRAINS FOR APPLICATION IN GASTROINTESTINAL DISEASES

(75) Inventors: Simone Guglielmetti, Milan (IT); Diego Mora, Milan (IT)

(73) Assignee: Naturewohl Pharma GmbH, Graefelfing (DE)

( * ) Notice: Subject to any disclaimer, the term of this patent is extended or adjusted under 35 U.S.C. 154(b) by 145 days.

(21) Appl. No.: 13/982,932

(22) PCT Filed: Jan. 27, 2012

(86) PCT No.: PCT/EP2012/051369
§ 371 (c)(1),
(2), (4) Date: Nov. 13, 2013

(87) PCT Pub. No.: WO2012/104226
PCT Pub. Date: Aug. 9, 2012

(65) Prior Publication Data
US 2014/0056852 A1   Feb. 27, 2014

(30) Foreign Application Priority Data
Jan. 31, 2011   (EP) .................................... 11000744

(51) Int. Cl.
*A61K 35/74*   (2015.01)
*A23L 1/30*    (2006.01)
*A61K 35/745*  (2015.01)

(52) U.S. Cl.
CPC ............ *A61K 35/745* (2013.01); *A23L 1/3014* (2013.01)

(58) Field of Classification Search
None
See application file for complete search history.

(56) References Cited

U.S. PATENT DOCUMENTS

2009/0274662 A1 * 11/2009 Magowan et al. ........... 424/93.4

FOREIGN PATENT DOCUMENTS

| EP | 1141235 B1 | 5/2006 |
|----|------------|--------|
| EP | 1930407 A1 | 6/2008 |
| EP | 2270133 A1 | 1/2011 |
| RU | 2152993 C1 | 7/2000 |
| RU | 2184146 C1 | 6/2002 |
| WO | WO-2009151329 A1 | 12/2009 |

OTHER PUBLICATIONS

Brenner et al. "Bifidobacterium Infantis 35624: A Novel Probiotic for the Treatment of Irritable Bowel Sndrome." Reviews in Gastroenterolgical Disorder vol. 9, No. 1 (2009) pp. 7-15.
Kassinen et al. "The Fecal Microbiota or Irritable Bowel Syndrome Patients Differs Significantly from that of Health Subjects." Gastroenterology 2007; 133:24-33.
Marshall et al. "Intestinal Permeability in Patients with Irritable Bowel Syndrome after a Waterborne Outbreak of Gastroenteritis in Walkerton, Ontario." Aliment Pharmacol Ther 2004; 1317-1322.
Whorwell et al. "Efficacy of an Encapsultated Probiotic Bifidobacterium infantis 35624 in Women with Irritable Bowel Syndrome." Am J Gastroenterol 2006; 101: 1581-1590.
O'Mahony et al. "Lactobacillus and Bifidobacterium in Irritable Bowel Syndrome: Symptom Responses and Relationship to Cytokine Profiles." Gastroenterology 2005;128: 541-551.
Kajander et al. "A Probiotic Mixture Alleviates Symptoms in Irritable Bowel Syndrome Patients: a Controlled 6-Month Intervention." Aliment Pharmacol Ther 2005; 22: 387-394.
Williams et al. "Clinical Trial: a Multi-strain Probiotic Preparation Significantly Reduces Symptoms of Irritable Bowel Syndrome in a Double-Blind Placebo-Controlled Study." Aliment Pharmacol Ther 29, 97-103.
Guyonnet et al. "Effect of a Fermented Milk Containing Bifidobacterium Animalis DN-173 010 on the Health-Related Quality of Life and Sympoms in Irritable Bowel Syndrome in Adults in Primary Care: a Multicentre, Randomized, Double-Blind, Controlled Trial." Aliment Pharmacol Ther 26, 475-486.
Guglielmetti et al. "Implication of an Outer Surface Lipoprotein in Adhesion of Bifidobacterium bifidum to Caco-2 Cells." Applied and Environmental Microbiology, Aug. 2008, p. 4695-4702.
Guglielmetti et al. "Study of the Adhesion of Bifidobacterium bifidum MIMBb75 to Human Intestinal Cell Lines." Curr Microbiol (2009) 59: 167-172.
Preising et al. "Selection of Bifidobacteria Based on Adhesion and Anti-Inflammatory Capacity In Vitro for Amelioration of Murine Colitis." Applied and Environmental Microbiology, May 2010, p. 3048-3051.
Wang et al. "Influence of Cell Surface Properties on Adhesion Ability of Bifidobacteria." World J Microbiol Biotechnol (2010) 26: 1999-2007.
Riedel et al. "Interaction of Bifidobacteria with Caco-2 Cells-Adhesion and Impact on Expression Profiles." International Journal of Food Microbiology 110 (2006) 62-68.

(Continued)

*Primary Examiner* — Robert Yamasaki
*Assistant Examiner* — Charles Zoltan Constantine
(74) *Attorney, Agent, or Firm* — Venable LLP; Keith G. Haddaway; Miguel A. Lopez

(57) ABSTRACT

The present invention provides a strain of *Bifidobacterium bifidum* or mutant or variant thereof showing at least an adhesion of about 10 bacterial cells per mm2 of epithelial cell monolayer or having at least an adhesion index of 1.5 and a strain of *Bifidobacterium bifidum* or mutant or variant thereof being *Bifidobacterium bifidum* MIMBb75, deposited under deposit No. DSM 24514, or a mutant or variant thereof for use as probiotic, in foodstuff and/or as a medicament. Further provided is a probiotic for mulation, comprising any of the strains, mutants or variants mentioned above, uses of said probiotic formulation, strains, mutants and variants thereof and a method for producing said probiotic formulation.

20 Claims, 8 Drawing Sheets

(56) References Cited

OTHER PUBLICATIONS

Alp et al. "The Role of Hemagglutination and Effect of Ecopolysaccharide Production on Bifidobacteroa Adhesion to Caco-2 Cells in Vitro." Microbiol Immunol 2010; 54: 658-665.
Gleinser et al. "Adhesion of an Anti-Inflammatory B. Bifidum Strain to Intestinal Epithelial Cells is Mediated by Proteinaceous Cell Wall Components." International Journal of Medical Microbiology; 61st Conference of the Deutschen-Gesellschaft-fur-Hygiene-Und-Mik Robiologie, Urban Und Fischer, DE; Göttingen, Germany, vol. 299, No. Suppl. 1, Sep. 1, 2009, p. 90.
Duffy et al. "Effectiveness of Bifidobacterium Bifidum in Mediating the Clinical Course of Murine Rotavirus Diarrhea." Pediatric Research vol. 35, No. 6, 1994. pp. 690-695.
Sanders, Mary Ellen. "Probiotics: Definitions, Sources, Selection, and Users." Clinical Infectious Diseases. 2008; 46: S58-61.
Si et al. "Intestinal Microecology and Quality of Life in Irritable Bowel Syndrome Patients." World J. Gastroenterol 2004; 10(12): 1802-1805.
Higgins et al. "Fast and Sensitive Multiple Sequence Alignments on a Microcomputer." vol. 5, No. 2 (1989) p. 151-153.
Kneifel, Wolfgang and Seppo Salminen (eds.) Probiotics and Health Claims. (Oxford: Wiley-Blackwell, 2011) [Directory Only].
Mattarelli et al. "Bifidobacterial Cell Wall Proteins in Bifidobacterium Globosum." Res. Microbiol. 1993, 144, 581-590.
Harada et al. *Essential involvement of Interlukin-8 in acute inflammation* J. Leukoc. Biol., 1994. 56: 559-564.
Mukaida, N. *Pathophysiological roles of interleukin-8 CXCL8 in pulmonary diseases* Am J Physiol Lung Cell Mol Physiol 2003. 284: L566-L577.
Moussavi & Adams, *An in Vitro Study on Bacterial Growth Interactions and Intestinal Epithelial Cell Adhesion Characteristics of Probiotic Combinations* Curr Microbiol, 2010. 60: 327-335.
Dinan et al.: "Enhanced Cholinergic-Mediated Increase in the Pro-Inflammatory Cytokine IL-6 in Irritable Bowel Syndrome: Role of Muscarinic Receptors", American Journal of Gastroenterology, 2008, p. 2570-2576.
Dinan et al.: "Hypothalamic-Pituitary-Gut Axis Dysregulation in Irritable Bowel Syndrome: Plasma Cytokines as a Potential Biomarker?", Gastroenterology, 2006, vol. 130, No. 2, 304-311.
Harada et al.: "Essential involvement of interleukin-8 (IL-8) in acute inflammation", Journal of Leukocyte Biology, vol. 56, 1994, p. 559-564.
Mazzucchelli et al.: "Expression of Interleukin-8 Gene Inflammatory Bowel Disease in Related to the Histological Grade of Active Inflammation", American Journal of Pathology, 1994, vol. 144, p. 997-1007.
Moussavi et al.: "An In Vitro Study on Bacterial Growth Interactions and Intestinal Epithelial Cell Adhesion Characteristics of Probiotic Combinations", Curr Microbiol, 2010, vol. 60, p. 327-335.
Niv et al.: "The efficacy of Lactobacillus reuteri ATCC 55730 in the treatment of patients with irritable bowel syndrome . . . ", Clinical Nutrition, 2005, vol. 24, p. 925-931.

* cited by examiner

BIFIDOBACTERIUM BIFIDUM STRAINS FOR APPLICATION IN GASTROINTESTINAL DISEASES

To date, diseases which are correlated with a functional disorder of the gastrointestinal tract and/or which are correlated with undesirable gastrointestinal inflammatory activity are common diseases with widespread prevalence. Diseases of both groups are characterized by abdominal pain, discomfort, distension, bloating, diarrhoea, constipation, digestive disorder, urgency and/or reduced and/or increased number of bowel movements, feeling of incomplete evacuation and/or combinations thereof, thereby leading to a significantly reduced overall wellbeing of the persons affected. In particular, with respect to irritable bowel syndrome (IBS) an efficient treatment is still lacking (Brenner and Chey, 2009). Several medications for IBS have been withdrawn or restricted due to adverse health effects. Additionally, current therapies are mainly targeted at single symptoms and do not alleviate IBS and improve quality of life (QoL) in general.

It is widely believed that diseases which are correlated with a functional disorder of the gastrointestinal tract, such as IBS or inflammatory bowel diseases, are accompanied (i) with an imbalance of the intestinal microbiota (Kassinen et al., 2007) and/or (ii) a dysfunctional intestinal barrier of the gastrointestinal tract (Marshall et al., 2004). This is thought to result in a reduction of probiotic bacteria, such as *Bifidobacteria*, in the gastrointestinal tract. Additionally, it is believed that a dysfunctional intestinal barrier causes undesirable entrance of facultative pathogenic bacteria into the mucosa which can lead to gastrointestinal inflammatory activity, subsequently. Recent studies propose that this inflammation triggers typical IBS symptoms such as pain, motility and dysfunction of the intestine.

An imbalance of the intestinal microbiota is mainly characterised by a reduced number of non-pathogenic microorganisms of human origin, such as *Bifidobacteria*, whereas the number of facultative pathogenic microorganisms, such as *Enterobacteria*, is increased (Jian-Min et al., 2004). This imbalance is believed to lead to an increased production of gaseous compounds and short-chain fatty acids, dysmotility, flatulence and pain of the persons affected. Thus, for bringing the intestinal microbiota back into balance, probiotic bacteria came into focus. They presumably have beneficial effects on immune function by means of competitive inhibition and may beneficially affect the host by improving the intestinal microbial balance. "Probiotics" comprising probiotic bacteria of non-pathogenic human origin have been defined as living microbial food and drugs which upon ingestion in certain numbers exert health effects beyond inherent basic nutrition. Mixtures of various microorganisms, particularly species of *Lactobacillus* and *Streptococcus*, have traditionally been used in fermented dairy products or drugs to promote health.

Many studies have been performed on this issue, however, as an imbalance of the intestinal microbiota is only one side of the coin, it is not surprising that most therapies which simply focus on the delivery of probiotics to the gastrointestinal tract, have not been successful in alleviating all symptoms of patients suffering from a functional disorder of the gastrointestinal tract. For example, IBS is diagnosed by the Rome III criteria, which are basically: abdominal pain or discomfort on at least 3 days per month during the last three months with symptoms which started at least 6 months ago combined with at least two criteria of (a) ease through defecation, (b) starting associated with a change in stool frequency or (c) in stool consistency and is often accompanied by bloating or distention, and bowel movement difficulties, either constipation and/or diarrhoea. Coming along with these symptoms, patients may suffer from impaired social and personal function and diminished quality of life. Nevertheless, even if the symptoms, such as pain/discomfort, distension/bloating, urgency are largely removed an improvement of the overall health related quality of life (QoL) of the patient is very desirable. To date, none of the treatments provided, including probiotics and others, have been able to improve the symptoms pain/discomfort, distension/bloating and digestive disorder simultaneously with the QoL.

In this respect, the second important aspect in the development of a functional disorder of the gastrointestinal tract has to be considered which concerns a dysfunctional intestinal barrier of the gastrointestinal tract characterised by an increased permeability thereof. One very popular theory in this respect is that perturbations in both, the gut and the systemic immune system allow pathogenic microorganisms—which might dominate in case of an imbalance of the intestinal microbiota—to pass the barrier and penetrate the mucosa, thereby causing inflammatory reactions. Based on this hypothesis, several studies have been performed which focus on the treatment and alleviation of the inflammatory reaction and its effects on the gastrointestinal tract. EP 1 141235 for example describes a *Bifidobacterium longum infantis* (*B. infantis*) strain UCC35624 for application in nutritional supplements and in drugs which showed a strong ability to stimulate an anti-inflammatory response in the host by decreasing IL-8 levels (Whorwell et al., 2006) and normalizing the IL-10/IL-12 ratio (O'Mahony et al., 2005). This ability is said to might be the major reason for the effect of *Bifidobacterium longum infantis* strain UCC35624 on IBS and symptoms of inflammatory bowel diseases. However, different sources question whether the effect of *B. infantis* can be attributed to direct anti-inflammatory properties. Further, although *Lactobacillus salivarius* has also shown strong anti-inflammatory effects in vitro and in mice model—comparable to *B. Infantis*—it has not shown significant effects in alleviating IBS and its symptoms.

Most important, the efficacy of probiotics is strongly strain specific and only certain strains might be able to improve IBS and its symptoms. Up to date, several studies have examined the effects of probiotics on symptoms of diseases which are correlated with a functional disorder of the gastrointestinal tract, such as IBS (O'Mahony et al., 2005, Kajander et al., 2005; Williams et al., 2008; Guyonnet et al., 2007). However, only a few could show a significant benefit. Additionally, no probiotic strain showed a significantly alleviating effect to symptoms of irritable bowel syndrome and a simultaneously improved quality of life. These findings could be attributed to the fact that the efficacy of probiotics is strongly strain specific. It is widely accepted that the properties of one probiotic strain cannot be transferred to another (Brenner and Chey, 2009). Therefore, it is important to acknowledge that the efficacy and effect of a single probiotic strain cannot be predicted which underlines the importance of testing and proving the efficacy of a single strain. For this purpose, methods are described in the experimental section.

Never before, a probiotic study has shown a reduction of the above mentioned symptoms (pain/distension/bloating/urgency/digestive disorder) and a simultaneous improvement of a patient's quality of life in a disease like IBS. Thus, there is a significant need for a therapy improving the symptoms pain/discomfort, distension/bloating, urgency and digestive disorder and the overall quality of life of a patient suffering from a functional disorder of the gastrointestinal tract, taking into account that the intestinal microbiota is brought back into balance and also the functionality of the intestinal wall is restored.

Therefore, the present invention provides a strain of *Bifidobacterium bifidum* (*B. bifidum*) or mutant or variant thereof for use as probiotic, in foodstuff and/or as a medicament, showing at least an adhesion of about 10 bacterial cells per mm$^2$ of epithelial cell monolayer or having at least an adhesion index of 1.5 and a strain of *Bifidobacterium bifidum* or mutant or variant thereof for use as probiotic, in foodstuff and/or as a medicament being *Bifidobacterium bifidum* MIMBb75, deposited under deposit No. DSM 24514, or a mutant or variant thereof which showed not only a significant improvement of the symptoms abdominal pain/discomfort, distension/bloating, urgency and/or digestive disorder of a gastrointestinal disease, in particular of IBS, but moreover simultaneously led to a significant gain in the quality of life of the patient. Further provided is a probiotic formulation and uses of the strain and the probiotic formulation. The alleviation of general IBS along with an improvement of the single symptoms pain/discomfort, distension/bloating, urgency and/or digestive disorder with a simultaneous improvement of QoL with the strains of the invention, such as a strain of *Bifidobacterium bifidum* or mutant or variant thereof showing at least an adhesion of about 10 bacterial cells per mm$^2$ of epithelial cell monolayer or having at least an adhesion index of 1.5 or a strain of *Bifidobacterium bifidum* or mutant or variant thereof being *Bifidobacterium bifidum* MIMBb75, deposited under deposit No. DSM 24514, or a mutant or variant thereof was an unexpected result as it is known and accepted in the prior art that the effectiveness of a probiotic is highly strain specific and even close related members of one *Bifidobacterium* strain species regularly do not have comparable properties or are even inactive in gastrointestinal diseases (Brenner and Chey, 2009). Without intention of being bound to one theory, the inventors believe that the exceeding and unexpected efficiency of the *Bifidobacterium bifidum* strain of the invention and in particular of *Bifidobacterium bifidum* MIMBb75 is due to its ability to prevent the passage of pathogenic bacteria through the intestinal barrier of the gastrointestinal tract and their penetration of the mucosa. Assuming that the dysfunction of the intestinal barrier is due to "holes" or weakened parts in the intestinal wall through which the pathogenic microorganisms might enter the mucosa, the inventors believe that adhesion of non-pathogenic cells to the intestinal wall reduce the permeability of the barrier thereby improving the intestinal wall in a "hole plugging" mode of action. In this way, the strain and probiotic formulation of the invention have a double positive effect on the gastrointestinal flora and health as not only inflammatory reactions of the mucosa are prevented but also the intestinal microbiota is brought back into balance. Further, it is very important that a reduction of the symptoms or the disease itself is also maintained during the washout-phase, i.e. the phase after end of therapy, wherein for example no further strain, mutant or variant thereof of the invention or probiotic formulation comprising the strain, mutant or variant thereof of the invention is administered to the subject or patient. In case of the strain, the mutant or variant of the invention, the positive effect of the strain, mutant or variant of the invention is maintained in case of global IBS symptoms, abdominal pain/discomfort, distension/bloating and digestive disorder during the washout-phase as will be explained in detail below and is also presented in the Example and Figure section.

Thus, the present invention provides a strain of *Bifidobacterium bifidum* or mutant or variant thereof for use as probiotic, in foodstuff and/or as a medicament, the strain or mutant or variant thereof showing at least an adhesion of about 10 bacterial cells per mm$^2$ of epithelial cell monolayer or having at least an adhesion index of 1.5. Preferably, said strain is *Bifidobacterium bifidum* MIMBb75, deposited under deposit No. DSM 24514, or a mutant or variant thereof. Also, provided is a strain of *Bifidobacterium bifidum* or mutant or variant thereof for use as probiotic, in foodstuff and/or as a medicament, the strain being *Bifidobacterium bifidum* MIMBb75, deposited under deposit No. DSM 24514, or a mutant or variant thereof. Said strain, mutant or variant is especially for use as probiotic, in foodstuff and/or as a medicament in the prophylaxis and/or treatment of a disease correlated with a functional disorder of the gastrointestinal tract, with undesirable gastrointestinal inflammatory activity, with an imbalance of the intestinal microbiota, a reduction of *Bifidobacteria* in the gastrointestinal tract and/or a dysfunctional intestinal barrier of the gastrointestinal tract, and/or for use in alleviating, preventing and/or treating a subject suffering from abdominal pain, discomfort, distension, bloating, urgency, digestive disorder, and/or reduced and/or increased number of bowel movements, feeling of incomplete evacuation, global IBS symptoms and/or combinations thereof or for improving the quality of life of a patient. The usefulness of the strain, mutant or variant as probiotic, in foodstuff and/or as a medicament in alleviating, preventing and/or treating a subject suffering from abdominal pain, discomfort, distension, digestive disorder, bloating, urgency and/or reduced and/or increased number of bowel movements, feeling of incomplete evacuation, global IBS symptoms and/or combinations thereof can be assessed using a 7-point Likert scale which is commonly used in clinical studies and will be further described below. The quality of life (QoL) of a patient may be assessed using the standard SF-12 questionnaire which is also common to a person skilled in the art an in clinical studies and an accepted standard to measure the QoL. Moreover, in case of global IBS symptoms, abdominal pain/discomfort, distension/bloating the positive effect of the strain, mutant or variant of the invention is maintained during the washout-phase as will be explained in detail below and is also presented in the Example and Figure section.

In one embodiment, the disease is a member selected from the group consisting of irritable bowel movement, inflammatory bowel disease, e.g. Crohn's disease or ulcerative colitis, irritable bowel syndrome, pouchitis or post infection colitis, gastrointestinal cancer, a systemic disease such as rheumatoid arthritis, an autoimmune disorders due to undesirable inflammatory activity, diarrhoeal disease due to undesirable inflammatory activity, such as *Clostridium difficile* associated diarrhoea, antibiotics associated diarrhoea, *Rotavirus* associated diarrhoea or post infective diarrhoea, and combinations thereof, preferably the disease is irritable bowel movement.

In one embodiment, the strain, mutant or variant of the invention is a genetically modified mutant or the strain, mutant or variant thereof is a naturally occurring variant. In alternative embodiments, the cells of the strain, mutant or variant are viable or non-viable. With non-viable cells product preparation is simpler, cells may be incorporated easily into pharmaceuticals and storage requirements are much less limited than in case of viable cells. Cells may be killed thermally or by exposure to altered pH or subjection to pressure. However, viable cells are able to inhabit the gastrointestinal system of a subject suffering from a disease or symptom as described herein, and thus have a higher efficacy in alleviating, preventing and/or treating a subject suffering from such disease or symptom.

The invention further provides a probiotic formulation comprising of the strain of *Bifidobacterium bifidum* or mutant or variant thereof for use as probiotic, in foodstuff and/or as a medicament, the strain or mutant or variant thereof showing at least an adhesion of about 10 bacterial cells per mm$^2$ of epithelial cell monolayer or having at least an adhesion index of 1.5, such as *Bifidobacterium bifidum* MIMBb75, deposited under deposit No. DSM 24514, or a mutant or variant thereof. Preferably, the probiotic formulation is for use as probiotic, in foodstuff and/or as a medicament.

In a preferred embodiment, the probiotic formulation further comprises at least one prebiotic. Preferably, the prebiotic is inulin or a fructooligosaccharide.

In any of the embodiments mentioned above, the probiotic formulation further comprises at least one pharmaceutically acceptable compound, an ingestible carrier, an adjuvant, a bacterial component, a drug entity, a biological compound and/or a protein and/or peptide, in particular a protein and/or peptide that is rich in glutamine/glutamate, a lipid, a carbohydrate, a vitamin, mineral and/or trace element; optionally said at least one pharmaceutically acceptable compound is a member selected from the group consisting of one or more vitamins, such as vitamins of the B group, one or more minerals, such as calcium or magnesium, one or more carbohydrates, such as lactose, maltodextrin, inulin, dextrose, mannitol, maltose, dextrin, sorbitol, fructose, and a mixture thereof. Preferably, the ingestible carrier is a capsule, tablet, powder or a food product; optionally the food product is a dairy product, acidified milk, yoghurt, frozen yoghurt, yoghurt production, such as fermented yoghurt drink, drinking yoghurt, cheese, fermented cream, milk based desserts fermented milk or humanised milk, milk powder, milk concentrate, cheese spread, dressing, beverage and others.

In one embodiment, the probiotic formulation further comprises a protein and/or peptide, in particular a protein and/or peptide that is rich in glutamine/glutamate, a lipid, a carbohydrate, a vitamin, mineral and/or trace element.

In any of the above embodiments, the strain, mutant or variant may be present in the probiotic formulation at more than $10^1$ cfu per capsule or tablet or per unit of powder or food product, optionally not less than $10^2$, $10^3$, $10^4$, $10^5$ or $10^6$ colony forming units (cfu) per capsule or tablet or per unit of powder or food product, preferably the strain, mutant or variant thereof is present at more than $10^7$ cfu per capsule or tablet or per unit of powder or food product, more preferably the strain, mutant or variant is present at more than $10^8$ cfu per capsule or tablet or per unit of powder or food product, even more preferably the strain, mutant or variant is present at more than $10^9$ cfu or more than $10^{10}$ cfu per capsule or tablet or per unit of powder or food product. A "unit of powder" denotes an amount of powder which comprises more than $10^1$ cfu, optionally not less than $10^2$, $10^3$, $10^4$, $10^5$ or $10^6$ colony forming units (cfu), preferably more than $10^7$ cfu, more preferably more than $10^8$ cfu, even more preferably more than $10^9$ cfu or more than $10^{10}$ cfu. Thus, a unit of powder represents the amount which comprises the standard daily dose of a patient, however, the daily dose may be increased or reduced due to several reasons and in several ways which are described below. A typical amount by weight of a unit of powder should be easily ingestible and digestible, ranging from mg to several gram, for example 5 g, 10 g, 15 g or more. A unit of powder may also be mixed with any food product mentioned herein and also with another food product which is regarded suitable by a person skilled in the art. Thus, the amount of cfu per amount by weight of powder may be much higher than the standard daily dose in an amount of powder which is regarded easily ingestible and digestible. Here, the powder will have to be diluted with other components allowed in the probiotic formulation as described above. A "unit of food product" or "food product" in general denotes a typical amount by weight or volume which is regarded as standard or typical quantity of the particular food product used as ingestible carrier, a typical amount proposed as consumption portion to be eaten or drunk, a packaging unit or comparable. A "unit of ingestible carrier" hence denotes a tablet, capsule, suppository or comparable or a unit of powder or unit of food product which denotes a typical amount by weight or volume which is regarded as standard or typical quantity of the particular food product used as ingestible carrier, a typical amount proposed as consumption portion to be eaten or drunk, a packaging unit or comparable.

In any of the above embodiments, the daily amount of the strain, mutant or variant administered to a patient in the probiotic formulation is not less than $10^1$ cfu per capsule or tablet or per unit of powder or food product, optionally not less than $10^2$, $10^3$, $10^4$, $10^5$ or $10^6$ cfu, preferably not less than $10^7$ cfu, more preferably not less than $10^8$ cfu, even more preferably not less than $10^9$ cfu or not less than $10^{10}$ cfu.

The probiotic formulation according to any of the above embodiments is useful and provided for use as probiotic, in foodstuff and/or as a medicament in the prophylaxis and/or treatment of a disease correlated with a functional disorder of the gastrointestinal tract, with undesirable gastrointestinal inflammatory activity, with a reduction of *Bifidobacteria* in the gastrointestinal tract and/or a dysfunctional intestinal barrier of the gastrointestinal tract, and/or for alleviating, preventing and/or treating a subject suffering from abdominal pain, discomfort, distension, bloating, digestive disorder, urgency and/or reduced and/or increased number of bowel movements, feeling of incomplete evacuation, global IBS symptoms and/or combinations thereof. Optionally, the disease is a member selected from the group consisting of irritable bowel movement, inflammatory bowel disease, e.g. Crohn's disease or ulcerative colitis, irritable bowel syndrome, pouchitis or post infection colitis, gastrointestinal cancer, a systemic disease such as rheumatoid arthritis, an autoimmune disorders due to undesirable inflammatory activity, diarrhoeal disease due to undesirable inflammatory activity, such as *Clostridium difficile* associated diarrhoea, antibiotics associated diarrhoea, *Rotavirus* associated diarrhoea or post infective diarrhoea, and combinations thereof. Preferably the disease is irritable bowel movement.

The invention also provides uses of the strain, mutant or variant of the invention and of the probiotic formulation of the invention as probiotic, in foodstuff and/or as a medicament in the prophylaxis and/or treatment of a disease correlated with a functional disorder of the gastrointestinal tract, with undesirable gastrointestinal inflammatory activity, with a reduction of *Bifidobacteria* in the gastrointestinal tract and/or a dysfunctional intestinal barrier of the gastrointestinal tract, and/or for alleviating, preventing and/or treating a subject suffering from abdominal pain, discomfort, distension, bloating, digestive disorder, urgency and/or reduced and/or increased number of bowel movements, feeling of incomplete evacuation and/or combinations thereof. Optionally, the disease is a member selected from the group consisting of irritable bowel movement, inflammatory bowel disease, e.g. Crohn's disease or ulcerative colitis, irritable bowel syndrome, pouchitis or post infection colitis, gastrointestinal cancer, a systemic disease such as rheumatoid arthritis, an autoimmune disorders due to undesirable inflammatory activity, diarrhoeal disease due to undesirable inflammatory activity, such as *Clostridium difficile* associated diarrhoea, antibiotics associated diarrhoea, *Rotavirus* associated diarrhoea or post infective diarrhoea, and combinations thereof.

Also provided is a method for producing the probiotic formulation of the invention, comprising at least the following steps:
a) fermenting and/or growing the strains or mutants or variants of the invention, preferably a strain or mutant or variant thereof showing at least an adhesion of about 10 bacterial cells per mm$^2$ of epithelial cell monolayer or having at least an adhesion index of 1.5, or the strain *Bifidobacterium bifidum* MIMBb75, deposited under deposit No. DSM 24514, or a mutant or variant thereof, in a protein-rich liquid growth medium,
b) harvesting the cells by centrifugation, stabilising, freeze-drying, milling and sieving of the cells,
c) optionally mixing/blending the cells with one or more members of the group consisting of a prebiotic, a pharmaceutically acceptable compound, an adjuvant, a bacterial component, a drug entity, a biological compound, a protein and/or peptide or else, and
d) introducing the cells of step b) or the mixture of step c) in an ingestible carrier.

The *Bifidobacterium bifidum* strain or mutant or variant thereof for use as probiotic, in foodstuff and/or as a medicament showing at least an adhesion of about 10 bacterial cells per mm$^2$ of epithelial cell monolayer or having at least an adhesion index of 1.5, such as *Bifidobacterium bifidum* MIMBb75 or a mutant or variant thereof, deposited under deposit No. DSM 24514, and the strain of *Bifidobacterium bifidum* or mutant or variant thereof for use as probiotic, in foodstuff and/or as a medicament being *Bifidobacterium bifidum* MIMBb75, deposited under deposit No. DSM 24514, or a mutant or variant thereof (both strains are referred to as the "strains" or the "cells" of the invention) belong to the genus of *Bifidobacteria* which are gram-positive, non-motile, often branched anaerobic bacteria generally present in the gastrointestinal tract and vagina. They are commonly isolated from the faeces of healthy infants and adults. If it is referred to the strains, also cells of the strain are meant. *Bifidobacteria* have already been describes to aid in digestion, are associated with a lower incidence of allergies and may also play a role in preventing some forms of tumour growth. *Bifidobacteria* belong to the family of *Bifidobacteriaceae* of *Actinobacteria*. *Bifidobacterium bifidum* MIMBb75 is obtainable from the Industrial Microbiology Culture Collection, DiSTAM, University of Milan, Milan, Italy and a deposit of *Bifidobacterium bifidum* MIMBb75 was made at the DSMZ (Deutsche Sammlung von Mikroorganismen und Zellkulturen GmbH, Braunschweig, Germany) on 26 Jan. 2011 and deposited under deposit No. DSM 24514. The strains, mutants or variants thereof of *Bifidobacterium bifidum* of the invention have inhibitory activity against a broad range of Gram positive and Gram negative bacteria. The strains of the invention of *Bifidobacterium bifidum* variants or mutants thereof exhibit a broad-spectrum of activity against bacteria including *Staphylococcus, Pseudomonas, Coliform* and *Bacillus* species. A "mutant" of the strain of the present invention denotes a strain of *Bifidobacterium bifidum* which has been modified, i.e. mutated by standard molecular biology techniques which are known to a person skilled in the art. A "variant" of the strain of the invention is a naturally occurring variant, i.e. a variant occurring in the gastrointestinal tract and vagina of healthy infants and adults, closely related *Bifidobacterium bifidum* strain. Both, the mutant and the variant of the strain of the invention resemble the same beneficial properties as the *Bifidobacterium bifidum* strain of the invention and in particular as *Bifidobacterium bifidum* strain MIMBb75 to patients suffering from any disease or symptom described herein. Both, the variant and the mutant are also regarded as DNA homologues of the strain. In the scope of the present invention, the term "homologue" is used in reference to strains which share a certain degree of "homology", i.e. "identity" or "similarity", on chromosomal DNA level. Many algorithms exist to determine this degree of homology or similarity. Preferably the homology can be determined by means of the Lasergene software of the company DNA star Inc., Madison, Wis. (USA), using the CLUSTAL method (Higgins et al., 1989, Comput. Appl. Biosci., 5 (2), 151). An organism which is "homologous" (=essentially similar) on chromosomal DNA level has at least 55% or 60%, preferably at least 65% or 70%, more preferably at least 75% or 80%, even more preferably at least 85% or 90%, and most preferably at least 92%, 94%, 95%, 96%, 97%, 98% or 99% homology on chromosomal DNA level.

A "disease" in the sense of the invention is any condition of a subject, also referred to as patient or human, that is altered in comparison to the condition of a subject which is regarded healthy. In general, a disease of the invention is correlated with a functional disorder of the gastrointestinal tract, with undesirable gastrointestinal inflammatory activity, with an imbalance of the intestinal microbiota, a reduction of *bifidobacteria* in the gastrointestinal tract, a dysfunctional intestinal barrier of the gastrointestinal tract and/or combinations thereof. Typical diseases which are addressed by the strains, mutants, variants, the probiotic formulation and the uses thereof are all diseases of the gastrointestinal tract or the digestive system, such as irritable bowel movement, inflammatory bowel disease, e.g. Crohn's disease or ulcerative colitis, irritable bowel syndrome, pouchitis or post infection colitis, gastrointestinal cancer, a systemic disease such as rheumatoid arthritis, an autoimmune disorders due to undesirable inflammatory activity, diarrhoeal disease due to undesirable inflammatory activity, such as *Clostridium difficile* associated diarrhoea, antibiotics associated diarrhoea, *Rotavirus* associated diarrhoea or post infective diarrhoea, or else and combinations thereof. A "symptom" or "individual symptom" in the sense of the invention is the way a disease of a subject is manifested, such as abdominal pain, discomfort, distension, bloating, digestive disorder, urgency and/or reduced and/or increased number of bowel movements, feeling of incomplete evacuation, global IBS symptoms and/or combinations thereof and an overall reduced quality of life. "Global IBS symptoms" comprise an overall assessment of all individual symptoms mentioned above regarding IBS. A "patient" (=person or human or animal) is a healthy or non-healthy subject which ingests the probiotic formulation of the invention or the strain of *Bifidobacterium bifidum* or mutant or variant thereof showing at least an adhesion of about 10 bacterial cells per mm$^2$ of epithelial cell monolayer or having at least an adhesion index of 1.5 or of a therapy with the strain of *Bifidobacterium bifidum* or mutant or variant thereof being *Bifidobacterium bifidum* MIMBb75, deposited under deposit No. DSM 24514, or a mutant or variant thereof for preventive reasons without suffering from any disease or any symptom mentioned herein, or which ingests the probiotic formulation of the invention or the strain of *Bifidobacterium bifidum* or mutant or variant thereof showing at least an adhesion of about 10 bacterial cells per mm$^2$ of epithelial cell monolayer or having at least an adhesion index of 1.5 or of a therapy with the strain of *Bifidobacterium bifidum* or mutant or variant thereof being *Bifidobacterium bifidum* MIMBb75, deposited under deposit No. DSM 24514, or a mutant or variant thereof, for treatment reasons as the patient, person, human or animal suffers from any disease or any symptom mentioned herein, such as a disease of the gastrointestinal tract or correlated with a functional disorder of the gastrointestinal tract, with undesirable gastrointestinal inflammatory activity, with an imbalance of the intestinal microbiota, a reduction of *Bifidobacteria* in the gastrointestinal tract and/or a dysfunctional intestinal barrier of the gastrointestinal tract, or a symptom, such as abdominal pain, discomfort, distension, bloating, digestive disorder, urgency and/or reduced and/or increased number of bowel movements, feeling of incomplete evacuation and/or combinations thereof or a reduced quality of life. Thus, a patient (=person) is in need of a new therapy such as of a therapy with the strain of *Bifidobacterium bifidum* or mutant or variant thereof showing at least an adhesion of about 10 bacterial cells per mm$^2$ of epithelial cell monolayer or having at least an adhesion index of 1.5 or of a therapy with the strain of *Bifidobacterium bifidum* or mutant or variant thereof being *Bifidobacterium bifidum* MIMBb75, deposited under deposit No. DSM 24514, or a mutant or variant thereof. A patient, person or subject may also be a person without having any of the above mentioned disease or symptom who An "adhesive strain" in the sense of the invention is a *Bifidobacteria bifidum* strain or mutant or variant thereof that has adhesive properties towards cells of the human colon and is thus able to bind to the cells of the human, or also animal, intestinal wall, thereby reducing the permeability of the gastrointestinal barrier and improving the intestinal wall in a "hole plugging" mode of action. A straightforward method to test is a *Bifidobacterium bifidum* strain or mutant or variant thereof for this property is given in the Example section. In this respect, a *Bifidobacterium bifidum* strain or mutant or variant thereof showing at least an adhesion of about 10, preferably of about 20, more preferably of about 30, even more preferably of about 40, most preferably of about 50 or 55 bacterial cells per mm$^2$ of epithelial cell monolayer or having at least an adhesion index of 1.5, preferably of at least 2, more preferably of at least 2.5, even more preferably of at least 3 is regarded as being an adhesive strain or mutant or variant thereof.

The probiotic formulation of the present invention is for use as probiotic, in foodstuff and/or as a medicament and comprises a strain or an adhesive strain of *Bifidobacterium bifidum* or mutant or variant thereof which shows at least an adhesion of about 10, preferably of about 20, more preferably of about 30, even more preferably of about 40, most preferably of about 50 or 55 bacterial cells per mm$^2$ of epithelial cell monolayer or has at least an adhesion index of 1.5, preferably of at least 2, more preferably of at least 2.5, even more preferably of at least 3 or the probiotic formulation of the present invention is for use as probiotic, in foodstuff and/or as a medicament and comprises a strain of *Bifidobacterium bifidum* or mutant or variant thereof being *Bifidobacterium bifidum* MIMBb75, deposited under deposit No. DSM 24514, or a mutant or variant thereof. The probiotic formulation of the present invention may also be regarded as pharmaceutical formulation. "Foodstuff" denotes in principle any form of substance or material that is ingestible and digestible by human and preferably also by animal. In general, this comprises substances or material which can be eaten or drunk to provide nutritional support for the body and/or pleasure. In case of human, these substances may be of plant, microbial or animal origin. In case of the present invention, in particular foodstuff is meant which comprises microbial organisms, in particular at least the strains of the present invention, and also other substances which are mentioned herein to be optionally comprised in the probiotic formulation, such as at least one pharmaceutically acceptable compound, an ingestible carrier, an adjuvant, a bacterial component, a drug entity, a biological compound and/or a protein and/or peptide, in particular a protein and/or peptide that is rich in glutamine/glutamate, a lipid, a carbohydrate, a vitamin, mineral and/or trace element; optionally said at least one pharmaceutically acceptable compound is a member selected from the group consisting of one or more vitamins, such as vitamins of the B group, one or more minerals, such as calcium or magnesium, one or more carbohydrates, such as lactose, maltodextrin, inulin, dextrose, mannitol, maltose, dextrin, sorbitol, fructose, and a mixture thereof. A "medicament" is in general not understood as foodstuff since a medicament is generally only administered to a human or patient in a certain condition which is not considered as a healthy condition but as a disease. Nevertheless, a medicament can also provide nutritional support for the body and/or pleasure such as in case of a person suffering from depression. Medicaments and therapeutic goods in general are subject to more strict regulations and approval processes. These approval processes are not necessary in case of a foodstuff which is understood as the main way of administration and main application of the strains, mutants or variants of the invention. As already explained above, a "probiotic" in the sense of the invention comprises probiotic bacteria of non-pathogenic human origin and has been defined as living microbial food and medical supplements which upon ingestion in certain numbers exert health effects beyond inherent basic nutrition. Mixtures of various microorganisms, particularly species of *Lactobacillus* and *Streptococcus*, have traditionally been used in fermented dairy products to promote health. The probiotic of the present invention comprises at least the adhesive *Bifidobacterium bifidum* strains of the invention or mutants or variants thereof or the *Bifidobacterium bifidum* MIMBb75 strain of the invention or mutants or variants thereof. However, also other strains, cells, mutants or variants of other species which have been regarded as being useful probiotics may be present in the probiotic formulation of the present invention as bacterial component. These are for example probiotic strains of the species *Lactobacillus, Bifidobacterium, Saccharomyces, Streptococcus* or mixtures thereof. Thus, a "bacterial component" denotes a viable or non-viable strain or cell of a probiotic strain as mentioned above and may further be used for compounds, such as biological molecules, polysaccharides, lipids or else of bacterial origin or being produced by bacterial fermentation or expression. Even dead material of any bacterial species may be understood as bacterial compound.

The probiotic formulation of the invention may further comprise at least one prebiotic or a combination of two, three, four or even more different prebiotics. A "prebiotic" in the sense of the invention is meant to serve as nutrient to the strains of the invention and to keep them in a viable and healthy state after thawing from freeze-drying. Per gram of microbial cells, i.e. per gram of strain, in general, 2-5 g, preferably ~2.5 g, more preferably at least 2.5 g, even more preferably at least 3 g, most preferably at least 4 g of prebiotic is necessary. In general, by humans non-digestible food ingredients, such as certain carbohydrates, are used as prebiotic. Examples for a prebiotic comprise carbohydrates, preferably oligosaccharides, inulin, fructooligosaccharides, galactooligosaccharides, psyllium, oligofructose, isomaltooligosaccharides xylooligosaccharides, soyoligosaccharides, maltodextrin, glucooligosaccharides, mannanoligosaccharides, arabinogalactan, arabinxylan, lactosucrose, gluconannan, lactulose, polydextrose, oligodextran, gentioligosaccharide, pectic oligosaccharide, xanthan gum, gum arabic, hemicellulose, resistant starch and its derivatives, and mixtures and/or combinations thereof.

The probiotic formulation of the invention may further comprise at least one pharmaceutically acceptable compound, at least one ingestible carrier, at least one adjuvant, at least one bacterial component, at least one drug entity, at least one biological compound and/or at least one protein and/or peptide, in particular a protein and/or peptide that is rich in glutamine/glutamate, a lipid, a carbohydrate, a vitamin, mineral and/or trace element.

A "pharmaceutically acceptable compound" denotes a liquid, solid or gaseous chemical or biological compound which is acceptable in a pharmaceutical composition or formulation characterised by a well tolerability by the human and also animal physiology and body being pharmacologically inactive or having no harmful effect on the physiology of the recipient. At least one, two, three, four, five or even more different pharmaceutically acceptable compounds may be present in the probiotic formulation of the invention in different amounts. The amount may be adjusted by the manufacturer according to the specific needs of the *Bifidobacterium bifidum* strain which is used and according to a certain application, way of administration or dosage regimen. Examples of pharmaceutically acceptable compounds include prebiotics, carbohydrates, lipids, vitamins, minerals, trace elements, amino acids, nucleic acids, maltodextrin, inulin, lactose, glucose, sucrose, maltose, dextrin, dextrose, fructose, sorbitol, fructooligosaccharide, mannitol, corn starch, crystalline cellulose, gum arabic, calcium phosphate, alginates, calcium silicate, microcrystalline cellulose, cellulose, polyvinyl pyrrolidone, tragacanth gum, gelatin, preferably bovine gelatin, syrup, aminosalicylate, sulfasalazine, 5-aminosalicylic acid, 4-aminosalicylic acid, benzalazine, dihydrochloride salt, olsalazine, balsalazide, bismuth sub salicylate, methyl cellulose, carboxymethyl cellulose, methylhydroxybenzoic acid esters, propylhydroxybenzoic acid esters, talc, magnesium stearates, inert polymers, water and mineral oils, iodine, magnesium, magnesium aspartate-ascorbate complex, magnesium amino acid chelate, zinc, zinc amino acid chelate, selenium, selenium amino acid complex, copper, copper amino acid chelate, manganese, manganese amino acid chelate, chromium, chromium polynicotinate, molybdenum, molybdenum amino acid chelate, potassium, potassium aspartate-ascorbate complex, choline, choline bitartrate, inositol, vanadium, vanadyl sulfate, boron, boron aspartate-citrate, citrus bioflavinoids, modified cellulose gum, silica, vegetarian stearine, titanium dioxide, magnesium stearate, preferably said at least one, two, three, four, five or even more pharmaceutically acceptable compound is a member selected from the group consisting of one or more vitamins, such as B vitamins, one or more minerals, such as magnesium and calcium, one or more carbohydrates, gelatin, preferably bovine gelatin, mannitol, dextrin, fructose, sorbitol, a prebiotic, maltose, maltodextrin, inulin, dextrose, iron, lactose and a mixture thereof. Moreover, the probiotic formulation may comprise pharmaceutically acceptable fillers, binders, lubricants, wetting agents, disintegrants, emulsifying agents, suspending agents, preservatives, sweetening agents and flavoring agents which are known to a person skilled in the art.

The probiotic formulation and the strains or mutant or variant thereof of this invention may be formulated such that after administration to a patient, the strain or cells are released rapidly, continuously or slowly. Examples of vitamins which may be comprised in the probiotic formulation of the invention are water-soluble and water-insoluble vitamins, such as vitamin A (e.g. retinol, retinal and carotenoids including beta carotene), vitamin $B_1$ (thiamine), vitamin $B_2$ (riboflavin), vitamin $B_3$ (e.g. niacin, niacinamide, nicotinamide), vitamin $B_5$ (pantothenic acid), vitamin $B_6$ (e.g. pyridoxine, pyridoxamine, pyridoxal) vitamin $B_7$ (biotin), vitamin $B_9$ (e.g. folic acid, folinic acid), vitamin $B_{12}$ (e.g. cyanocobalamin, hydroxycobalamin, methylcobalamin), vitamin C (ascorbic acid), vitamin D (e.g. ergocalciferol, cholecalciferol), vitamin E (e.g. tocopherols, tocotrienols), vitamin K (e.g. phylloquinone, menaquinones), preferably vitamins of the B group are comprised in the probiotic formulation of the invention, such as vitamin $B_1$ (thiamine), vitamin $B_2$ (riboflavin), vitamin $B_3$ (e.g. niacin, niacinamide, nicotinamide), vitamin $B_5$ (pantothenic acid), vitamin $B_6$ (e.g. pyridoxine, pyridoxamine, pyridoxal) vitamin $B_7$ (biotin), vitamin $B_9$ (e.g. folic acid, folinic acid), vitamin $B_{12}$ (e.g. cyanocobalamin, hydroxycobalamin, methylcobalamin) and mixtures thereof. Examples of minerals comprised in the probiotic formulation of the invention are magnesium, calcium, zinc, selenium, iron, copper, manganese, chromium, molybdenum, potassium, vanadium, boron, titanium, preferably magnesium and/or calcium are present. A "trace element" is a chemical element which is only needed in very low quantities for the growth, development and/or physiology of the organism, preferably of a human organism. "Carbohydrates" are organic compounds consisting only of carbon, hydrogen and oxygen and having the empirical formula $C_m(H_2O)_n$, wherein the hydrogen to oxygen atom ratio is 2:1. "Lipids" are at least partially water-insoluble biological compounds due to a long hydrophobic carbohydrate part. Lipids are very important party of cell membranes in biological systems.

An "ingestible carrier" in the sense of the invention is a carrier which is used for administration of the probiotic formulation or the strain or mutant or variant thereof of the invention to a subject or patient helping to ingest the probiotic formulation and the strains or mutant or variant thereof of the invention. The term "dairy product" as used herein is meant to include a medium comprising milk of animal and/or vegetable origin. Milk of animal origin includes milk from cow, sheep, goat and buffalo. As milk of vegetable origin there can be mentioned any fermentable substance of vegetable origin which can be used according to the invention, in particular originating from soybeans, rice or cereals. A possible ingestible carrier is a member selected from the group comprising a capsule, tablet, powder, granule, troche, cachet wafer capsule, elixir, emulsion, solution, syrup, suspension, soft and hard gelatin capsule, suppository, aseptic packed powder or a food product; optionally the food product is a dairy product, acidified milk, yoghurt, frozen yoghurt, yoghurt production, such as fermented yoghurt drink, drinking yoghurt, cheese, fermented cream, milk based desserts fermented milk or humanised milk, milk powder, milk concentrate, cheese spread, dressing, beverage and others. An "adjuvant" in the sense of the invention is a pharmacological or immunological agent that modifies the effect of other agents, such as drugs or vaccines or of the probiotic formulation, strain or mutant or variant thereof of the present invention while having few—if any—direct effects when given alone.

"Drug entity" relates to a chemical or biological compound that is pharmaceutically active while being pharmaceutically tolerable to the patient, such as bisacodyl, loperamide, aminosalicylate, sulfasalazine, 5-aminosalicylic acid, 4-aminosalicylic acid, benzalazine, dihydrochloride salt, olsalazine, balsalazide, bismuth sub salicylate or mixtures thereof. Such compound may be any compound that promotes the beneficial effects of the probiotic formulation or strain, mutant or variant thereof of the invention either directly or indirectly. Directly means that the strain of *Bifidobacterium bifidum* or mutant or variant thereof itself is protected, its growth or adhesion to the intestinal barrier is supported. Indirectly means that additional substances or compounds, i.e. drug entities, which are known to be useful in prophylaxis and/or treatment of a disease correlated with a functional disorder of the gastrointestinal tract, with undesirable gastrointestinal inflammatory activity, with an imbalance of the intestinal microbiota, a reduction of *Bifidobacteria* in the gastrointestinal tract and/or a dysfunctional intestinal barrier of the gastrointestinal tract, or for use in alleviating, preventing and/or treating a subject suffering from abdominal pain, discomfort, distension, bloating, digestive disorder, urgency and/or reduced and/or increased number of bowel movements, feeling of incomplete evacuation and/or combinations thereof or for improving the quality of life of a patient may be comprised alone or in combination with other drug entities in the probiotic formulation. In particular, a drug entity may be comprised in the probiotic formulation which is a known medicament for treating diseases of the gastrointestinal tract, such as irritable bowel movement, inflammatory bowel disease, e.g. Crohn's disease or ulcerative colitis, irritable bowel syndrome, pouchitis or post infection colitis, gastrointestinal cancer, a systemic disease such as rheumatoid arthritis, an autoimmune disorders due to undesirable inflammatory activity, diarrhoeal disease due to undesirable inflammatory activity, such as *Clostridium difficile* associated diarrhoea, antibiotics associated diarrhoea, *Rotavirus* associated diarrhoea or post infective diarrhoea, and combinations thereof. Examples of such a drug entity known to a person skilled in the art and may be found in Rote Liste, 2010, Germany, or any other pharmaceutical register. A "biological compound" may be any biological compound such as a carbohydrate, amino acid, lipid, nucleic acid, protein, peptide, cell compartment, phospholipids, polyether, plant, animal, or microbial compound. "Protein", "peptide" or "polypeptide" is to be understood according to their general meaning being a linear composition of proteinogenic or non-proteinogenic amino acids, wherein proteins may also comprise one or more subunits and catalytically relevant substances, such as vitamins, minerals or substances.

"Colony forming unit" (cfu) is a measure of viable bacterial cells of the strain of *Bifidobacterium bifidum* or mutant or variant thereof of the invention. The probiotic formulation of the invention comprises the strain, mutant or variant thereof at more than $10^1$ cfu, optionally not less than $10^2$, $10^3$, $10^4$, $10^5$ or $10^6$ colony forming units (cfu) per capsule or tablet or per unit of powder or food product, preferably the strain, mutant or variant is present at more than $10^7$ cfu per capsule or tablet or per unit of powder or food product, more preferably, the strain, mutant or variant is present at more than $10^8$ cfu per capsule or tablet or per unit of powder or food product, even more preferably, the strain, mutant or variant is present at more than $10^9$ cfu per capsule tablet or per unit of powder or food product. The daily amount of the strain, mutant or variant thereof administered to a patient in the probiotic formulation is not less than $10^1$ cfu, optionally not less than $10^2$, $10^3$, $10^4$, $10^5$ or $10^6$ cfu, preferably not less than $10^7$ cfu, more preferably not less than $10^8$ cfu, even more preferably not less than $10^9$ cfu or less than $10^{10}$ cfu. The daily amount may be increased depending on the physiological condition of the patient, i.e. in case of severe symptoms. Here, the amount may be increased in that the daily amount is doubled, tripled or multiplied. On the contrary, the daily amount may be reduced, halved or divided by two, three or four, for example in case of intolerance or additional medication or the daily amounts as mentioned before may not be administered daily but every second or third day or weekly. The strain, mutant or variant thereof or the probiotic formulation may be taken at any time which is regarded convenient by the person or patient, such as in the morning, midday, in the afternoon or in the evening, preferably, the time is in the morning, for example after wake up, or in the evening, for example before going to sleep. If the strain, mutant or variant thereof or the probiotic formulation comprises an ingestible carrier being a food product, the administration is performed according to the nature of the ingestible carrier, i.e. food product. If the strain, mutant or variant thereof or the probiotic formulation comprises an ingestible carrier such as a capsule of tablet or comparable ingestible carrier, the administration is performed orally accompanied by a beverage or water, preferably by water.

In general, the probiotic formulation and the strains of the invention are administered according to the specific form of the probiotic, foodstuff or medicament. Thus, normally, the probiotic formulation and the strains of the invention are administered orally, preferably parenterally, or through the rectum.

The method for producing the probiotic formulation of the invention comprises at least the following steps:

a) fermenting and/or growing of a strain of *Bifidobacterium bifidum* or mutant or variant thereof showing at least an adhesion of about 10 bacterial cells per mm² of epithelial cell monolayer or having at least an adhesion index of 1.5 or a strain of *Bifidobacterium bifidum* or mutant or variant thereof being *Bifidobacterium bifidum* MIMBb75, deposited under deposit No. DSM 24514, or a mutant or variant thereof in a protein-rich liquid growth medium, b) harvesting the cells of the above mentioned strains by centrifugation, stabilising, freeze-drying, milling and sieving of the cells, c) optionally mixing/blending the cells with one or more members of the group consisting of a prebiotic, a pharmaceutically acceptable compound, an adjuvant, a bacterial component, a drug entity, a biological compound, a protein and/or peptide, and d) introducing the cells of step b) or the mixture of step c) in an ingestible carrier.

First it should be noted that fermentation and growing of *Bifidobacterium bifidum* strains, mutants or variants of the invention may be performed by standard means and methods which are known to a person skilled in the art, such as described in "Probiotics and Health Claims", Wolfgang Kneifel, Seppo Salminen, John Wiley & Sons; 1. Edition (7 Jan. 2011).

In general, a medium for growing and/or fermenting the *Bifidobacterium bifidum* strains, mutants or variants of the invention comprises at least water, dextrose, yeast extract and minerals. The standard medium used for growing and/or fermenting the strains or variants or mutants thereof of the invention is MRS broth (Difco, Detroit, Mich., USA) supplemented with 0.05% L-cysteine hydrochloride (cMRS). The skilled person is well aware of the fact that also other media may be used for growing, fermenting and pre-culture of bacterial organisms, such as strains of *Bifidobacterium bifidum*. Optionally, prior to step a) the strains or variants or mutants thereof are grown in a pre-culture in a shake flask. For this purpose, a volume of at least 200 mL, preferably of at least 300 mL, more preferably of at least 400 mL, even more preferably of at least 500 mL and most preferably of at least 600 mL of standard medium as mentioned above is inoculated with at least a single cell of the strain or variant or mutant thereof. This pre-culture is generally grown over night anaerobically at 37° C. at 220 rpm.

The pre-culture may completely or partially then be used for inoculation of a higher fermentation in a pre-fermenter in a volume of at least 500 L, preferably of at least 600 L, more preferably of at least 700 L, even more preferably of at least 800 L, most preferably of at least 1000 L. After fermentation of the strains, variants and mutants of the invention in a pre-fermenter, the cell culture containing said strains, variants and mutants is at least partially transferred to the main fermenter having at least a volume of at least 5000 L, preferably of at least 7500 L, more preferably of at least 10,000 L, even more preferably of at least 15,000 L and most preferably of at least 20,000 L. Also in the pre-fermenter and main fermenter, the above mentioned standard medium is used for fermentation and growing of the *Bifidobacterium bifidum* strains, mutants and variants thereof of the invention. Fermentation and growing is stopped and the cells are harvested after depletion of the carbohydrates comprised in the medium which serve as nutrient for the strains, mutants and variants of the invention. In general, the cell density after depletion is at least $10^1$ cfu, optionally not less than $10^2$, $10^3$, $10^4$, $10^5$ or $10^6$ cells/mL, preferably at least $10^7$ cells/mL, more preferably at least $10^8$ cells/mL, even more preferably at least $10^9$ cells/mL or at least $10^{10}$ cells/mL. The skilled person know methods for cell density or biomass determination, such as biomass determination as dry weight using standard drying procedures and gravimetric determination of preweighted glass tubes or by measurement of the optical density using a spectrophotometer (such as Hitachi U-1100, Japan) at an absorption of 578 nm.

The pre-fermenter and main fermenter may be derived from a standard bioreactor suitable for culturing, fermenting, growing and/or processing of a strain, mutant and/or variant of a strain of *Bifidobacterium bifidum* of the invention. Suppliers of standard bioreactors are, for example, Applikon Biotechnology B.V. (Schiedam, The Netherlands), Infors (Bottmingen, Switzerland), Bioengineering (Wald, Switzerland) and Sartorius Stedim Biotech GmbH (Göttingen, Germany). Both, pre-fermentation and main fermentation are performed in batch mode which means generally that no medium or other components are replenished during fermentation.

After main fermentation, the cells are harvested by centrifugation, such as by using a disc centrifuge or separator having an operating capacity of around 2000-15,000 L/h as provided by GEA Westfalia Separator Group GmbH (Oelde, Germany) or else. The cells are stabilised, freeze-dried, milled and sieved using standard applications and means which are well known to a person skilled in the art, subsequently. Freeze-drying gives a concentrate having a volume of 500 L to 1,000 L, preferably of 600 L to 800 L and having a weight of approximately 100 kg to 200 kg, preferably of ~150 kg.

Afterwards, the cells are optionally mixed with a prebiotic and/or at least one or more members of the group consisting of a pharmaceutically acceptable compound, an ingestible carrier, an adjuvant, a bacterial component, a drug entity, a biological compound and/or a protein and/or peptide and/or mixtures thereof, in particular a protein and/or peptide that is rich in glutamine/glutamate, a lipid, a carbohydrate, a vitamin, mineral and/or trace element; optionally said at least one pharmaceutically acceptable compound is a member selected from the group consisting of one or more vitamins, such as vitamins of the B group, one or more minerals, such as calcium or magnesium, one or more carbohydrates, such as lactose, maltodextrin, inulin, dextrose, mannitol, maltose, dextrin, sorbitol, fructose, and a mixture thereof in different amounts.

For obtaining the probiotic formulations of the invention, in general, 15-40 g, preferably 18-35 g, more preferably 20-30 g, even more preferably 22-28 g, most preferably 25 g of *Bifidobacterium bifidum* cells, strain, mutant or variant thereof of the invention are mixed with 50-100 g, preferably with 60-90 g, more preferably with 65-85 g, even more preferably with 70-80 g, most preferably with 75 g of one or more members of the group consisting of a prebiotic, carbohydrate, a pharmaceutically acceptable compound or mixtures thereof as nutrient for the of cells, strain, mutant or variant thereof, and are optionally mixed with 30-70 g, preferably with 35-65 g, more preferably with 40-60 g, even more preferably with 45-55 g, most preferably with 50 g of one or more members of the group consisting of a pharmaceutically acceptable compound, an ingestible carrier, an adjuvant, a bacterial component, a drug entity, a biological compound and/or a protein and/or peptide, in particular a protein and/or peptide that is rich in glutamine/glutamate, a lipid, a carbohydrate, a vitamin, mineral, trace element and or mixtures thereof for improvement of the pourability of the probiotic formulation. Preferably, 15-40 g, preferably 18-35 g, more preferably 20-30 g, even more preferably 22-28 g, most preferably 25 g of *Bifidobacterium bifidum* cells, strain, mutant or variant thereof of the invention are mixed with 50-100 g, preferably with 60-90 g, more preferably with 65-85 g, even more preferably with 70-80 g, most preferably with 75 g of a carbohydrate, carbohydrate mixture, prebiotic or mixture thereof, and optionally with 30-70 g, preferably with 35-65 g, more preferably with 40-60 g, even more preferably with 45-55 g, most preferably with 50 g of one or more members of the group consisting of a pharmaceutically acceptable compound, a carbohydrate, a vitamin, mineral, trace element and or mixtures thereof. More preferably, 15-40 g, preferably 18-35 g, more preferably 20-30 g, even more preferably 22-28 g, most preferably 25 g of *Bifidobacterium bifidum* cells, strain, mutant or variant thereof of the invention are mixed with 50-100 g, preferably with 60-90 g, more preferably with 65-85 g, even more preferably with 70-80 g, most preferably with 75 g of a carbohydrate, inulin, a fructooligosaccharide or a mixture thereof, and optionally with 30-70 g, preferably with 35-65 g, more preferably with 40-60 g, even more preferably with 45-55 g, most preferably with 50 g of one or more members of the group consisting of a vitamin, such as a vitamin of the B group, one or more minerals, such as calcium or magnesium, one or more carbohydrates, such as lactose, maltodextrin, inulin, dextrose, mannitol, fructooligosaccharide, mannit, maltose, dextrin, sorbitol, fructose, and a mixture thereof. Even more preferably, 25 g of *Bifidobacterium bifidum* cells, strain, mutant or variant thereof of the invention are mixed with 75 g of a member selected from the group consisting of a carbohydrate, prebiotic, maltodextrin, inulin, dextrose, mannitol, maltose, dextrin, sorbitol, fructose, and a mixture thereof, and are mixed with 50 g of a member selected from the group consisting of cellulose, pharmaceutically acceptable compound, an ingestible carrier, an adjuvant, a bacterial component, a drug entity, a biological compound and/or a protein and/or peptide, in particular a protein and/or peptide that is rich in glutamine/glutamate, a lipid, a carbohydrate, a vitamin, mineral, trace element and a mixture thereof. Most preferably, 25 g of *Bifidobacterium bifidum* cells, strain, mutant or variant thereof of the invention are mixed with 75 g maltodextrin, and are mixed with 50 g of cellulose. Mixing/blending the components with the cells, strain, mutant or variant thereof of the invention after fermenting and/or growing the strain, harvesting, stabilising, freeze-drying, milling and sieving, may be performed by standard techniques, applications and means which are known to a person skilled in the art, preferably a column blender is used. Of course, also higher or lower amounts can be used in mixing/blending depending on the volume of the device used for mixing/blending as long as the ratio of the components corresponds to the ratios mentioned above. A typical ratio for example is 25% strain, 75% prebiotic or carbohydrate or maltodextrin and 50% pharmaceutically acceptable compound, such as cellulose. For example, 50 mg-300 mg, preferably 75 mg-250 mg, more preferably 100 mg-200 mg, even more preferably 120 mg-175 mg, most preferably 150 mg of the *Bifidobacterium bifidum* cells, strain, mutant or variant thereof of the invention or of the above mentioned mixtures or probiotic formulations of the invention are introduced into one unit of ingestible carrier, for example into a capsule, tablet, troche, cachet wafer capsule, elixir, emulsion, solution, syrup, suspension, soft and hard gelatin capsule, suppository, aseptic packed powder or a food product, such as a dairy product, acidified milk, yoghurt, frozen yoghurt, yoghurt production, such as fermented yoghurt drink, drinking yoghurt, cheese, fermented cream, milk based desserts fermented milk or humanised milk, milk powder, milk concentrate, cheese spread, dressing, beverage and others, preferably 50 mg, preferably 75 mg, more preferably 100 mg, even more preferably 120 mg and most preferably 150 mg of the *Bifidobacterium bifidum* cells, strain, mutant or variant thereof of the invention or of the above mentioned mixtures are introduced into a capsule, tablet troche, cachet wafer capsule, soft and hard gelatin capsule, suppository, more preferably into a capsule, soft and hard gelatin capsule. Thereby, after introduction into the unit of ingestible carrier, i.e. the capsule, tablet, powder, granule, troche, cachet wafer capsule, elixir, emulsion, solution, syrup, suspension, soft and hard gelatin capsule, suppository, aseptic packed powder or food product, such as a dairy product, acidified milk, yoghurt, frozen yoghurt, yoghurt production, such as fermented yoghurt drink, drinking yoghurt, cheese, fermented cream, milk based desserts fermented milk or humanised milk, milk powder, milk concentrate, cheese spread, dressing and/or beverage comprises more than $10^1$ cfu, optionally not less than $10^2$, $10^3$, $10^4$, $10^5$ or $10^6$ cfu, preferably more than $10^7$ cfu, more preferably more than $10^8$ cfu, even more preferably more than $10^9$ cfu or more than $10^{10}$ cfu. In any case the amount by weight may be adjusted according to the concentration of cfu, so that the amount of the *Bifidobacterium bifidum* cells, strain, mutant or variant thereof of the invention in the final product, such as capsule, tablet, powder, granule, troche, cachet wafer capsule, elixir, emulsion, solution, syrup, suspension, soft and hard gelatin capsule, suppository, aseptic packed powder or food product corresponds to more than $10^1$ cfu, optionally not less than $10^2$, $10^3$, $10^4$, $10^5$ or $10^6$ cfu, preferably more than $10^7$ cfu, more preferably more than $10^8$ cfu, even more preferably more than $10^9$ cfu or more than $10^{10}$ cfu. In case that the amount of cfu is less than $10^1$ cfu, optionally not less than $10^2$, $10^3$, $10^4$, $10^5$ or $10^6$ cfu, $10^7$ cfu, $10^8$ cfu, even $10^9$ cfu or less than $10^{10}$ cfu, the patient may adapt to aforementioned amounts of cfu by administering more than one unit of ingestible carrier.

In an exemplary embodiment, 25 mg of *Bifidobacterium bifidum* MIMBb75 deposited under deposit No. DSM 24514 cells, i.e. at least $10^9$ cfu *Bifidobacterium bifidum* MIMBb75 deposited under deposit No. DSM 24514, 75 mg maltodextrin and 50 mg cellulose are introduced into one gelatine capsule, preferably in a bovine gelatine capsule. Preferably, the aforementioned described capsule with 25 mg of *Bifidobacterium bifidum* MIMBb75 deposited under deposit No. DSM 24514 cells, comprises at least $10^9$ cfu *Bifidobacterium bifidum* MIMBb75 deposited under deposit No. DSM 24514, 75 mg maltodextrin and 50 mg cellulose is administered once daily. Ingestible carriers in general should be of standard to high quality, should fulfil the hygiene requirements of food supplements and may be obtained from various manufacturers. Capsules, for example bovine gelatine capsules, may for example be obtained from Capsugel (Bornem, Belgium).

In another preferred embodiment, 25 mg of *Bifidobacterium bifidum* MIMBb75 deposited under deposit No. DSM 24514 cells, preferably comprising at least $10^9$ cfu *Bifidobacterium bifidum* MIMBb75 deposited under deposit No. DSM 24514 and 2 g maltodextrin are mixed and are considered as unit of powder. Preferably, the aforementioned described unit of powder with 25 mg of *Bifidobacterium bifidum* MIMBb75 deposited under deposit No. DSM 24514 cells, i.e. at least $10^9$ cfu *Bifidobacterium bifidum* MIMBb75 deposited under deposit No. DSM 24514 is administered once daily.

Independent of the particular ingestible carrier chosen by the person or patient, the daily amount of the *Bifidobacterium bifidum* cells, strain, mutant or variant administered to a patient in the probiotic formulation is not less than $10^1$ cfu, optionally not less than $10^2$, $10^3$, $10^4$, $10^5$ or $10^6$ cfu, preferably not less than $10^7$ cfu, more preferably not less than $10^8$ cfu, even more preferably not less than $10^9$ cfu or not less than $10^{10}$ cfu. Alternative doses are discussed above.

The invention is not limited to the embodiments hereinbefore described which may be varied in detail.

EXAMPLES

1. Bacterial Culture Conditions

In general, *Bifidobacterium* species, such as *Bifidobacterium bifidum* MIMBb75, were routinely grown overnight anaerobically at 37° C. in MRS broth (Difco, Detroit, Mich., USA) supplemented with 0.05% L-cysteine hydrochloride (cMRS).

2. Test for Adhesive Properties of *Bifidobacterium bifidum* MIMBb75 to Caco-2 Human Intestinal Epithelial Cell Lines 2.1 Bacterial Adhesion to Caco-2 cells This test can be performed to test whether a certain *Bifidobacteria* strain has adhesive properties towards cells of the human colon and are thus to be understood as adhesive strain in the sense of the present invention. Human colon adenocarcinoma Caco-2 cells (ATCC HTB-37) were routinely grown in 3-cm petri plates on microscopy cover glasses in Dulbecco's modified Eagle's medium supplemented with 10% (vol/vol) heat-inactivated (30 min at 56° C.) foetal calf serum, 100 U mL$^{-1}$ penicillin, 100 mg mL$^{-1}$ streptomycin, 0.1 mM nonessential amino acids, and 2 mM L-glutamine and incubated at 37° C. in a water-jacketed incubator in an atmosphere of 95% air and 5% carbon dioxide. For this test, epithelial cells from any in vivo source, including but not limited to epithelial cells derived from the human gastrointestinal tract are suitable, however, CaCo-2 cells, or derivatives thereof, are most preferred, and are available commercially from culture collection banks such as the ATCC and ECACC. The culture medium was changed twice weekly. For adhesion assays, cells were used 15 days after confluence (fully differentiated cells). Cell monolayers were carefully washed twice with phosphate-buffered saline (PBS) (pH 7.3) before bacterial cells were added. The bacterial cell concentration of a culture grown overnight was determined microscopically after DAPI (4',6'-diamidino-2-phenylindole) staining. Approximately $2 \times 10^8$ cells of each strain resuspended in PBS (pH 7.3) were incubated with a monolayer of fully differentiated Caco-2 cells. After 1 h at 37° C. in anaerobic conditions, all monolayers were washed three times with PBS to release unbound bacteria. Cells were then fixed with 3 mL of methanol and incubated for 8 min at room temperature. After methanol was removed, cells were stained with 3 mL of Giemsa stain solution (1:20) (Carlo Erba, Milan, Italy) and left for 30 min at room temperature. Wells were then washed until no colour was observed in the washing solution and dried in an incubator for 1 h. Microscopy cover glasses were then removed from the petri plate and examined microscopically (magnification, ×100), immersed in oil. Adherent bacteria in 20 randomly selected microscopic fields were counted and averaged. An unpaired Student t test was run for statistically significant differences.

Bifidobacterium bifidum MIMBb75 was found to be well adherent to Caco-2 human colonic cells as a significant proportion of cells of this bacterial strain remained attached to the Caco-2 monolayer, providing evidence that the adhesion was not only nonspecific physical entrapment. In particular, about 55 bacterial cells adhered to a 1-$mm^2$ epithelial cell monolayer, resulting in an adhesion index (bacterial cells/100 Caco-2 cells) of 3,874 ($P<0.026$). In this respect, cells of a Bifidobacterium strain showing at least an adhesion of about 10 bacterial cells per $mm^2$ of epithelial cell monolayer or have at least an adhesion indexes of 1.5 are regarded as being an adhesive strain.

2.2 Preparation of Bacterial Cell Wall Extract

Bacterial cells from 0.2 L of liquid culture were harvested by centrifugation and processed according to methods described previously by Mattarelli et al. (1993) with a modified use of the French press (12,000 $lb/in^2$, ~2,142 $kg/cm^2$) for breaking cells.

3. Double-Blind, Randomized and Placebo-Controlled Study to Assess the Efficiency of Bifidobacterium bifidum MIMBb75 in Patients Having Irritable Bowel Syndrome

3.1 Overview 122 patients were successfully randomised to receive either placebo (N=62) or Bifidobacterium bifidum MIMBb75 (N=60) (also regarded as "Bifidobacteria group"). Subjects consumed either $1\times10^9$ cfu/capsule or placebo once a day for four weeks. The severity of IBS and individuell IBS symptoms was recorded daily on a 7-point Likert scale.

3.2 Study Population

Patients were recruited from principal investigators and by advertisement. The nutritional study protocol has been presented to the Ethics Committee of the Bavarian Chamber of Physicians. For inclusion, clinically inconspicuous subjects aged between 18 and 68 years with mild to moderate IBS (Rome III criteria) have been considered. Individuals with inflammatory organic gastrointestinal disease, systemic diseases, cancer, autoimmune diseases, diabetes, known lactose intolerance or immunodeficiency, known further abdominal surgery except appendectomy, no disease free sigmoidoscopy or coloscopy in the last five years when older 50 years, diagnosed hyperthyroidism, use of antipsychotics or systemic corticosteroids for at least 3 months prior to study start, major psychiatric disorder, celiac disease or pregnancy had been excluded.

3.3 Study Design

This study was performed as a prospective, multi-centre, randomised, double-blind, placebo-controlled, two-arm nutritional study. Throughout the study, patients recorded daily their global IBS symptoms as well as individual IBS symptoms using a patient diary. Additionally, patients have been questioned at physician site for global and individual IBS symptoms (visit 2-4) and quality of life (visit 3 and 4). Physician visits took place at screening, after two weeks (run-in phase), after 6 weeks (end of treatment) and after 8 weeks (end of wash-out phase) (FIG. 1).

After patients have given their written informed consent, they qualified for the screening examination at day 1 (visit 1), which included a complete medical history and physical examination. A blood sample was taken for analysis in a central laboratory, including a pregnancy test. At the screening visit, patients were instructed to maintain their eating and life style habits throughout the study. A patient diary has been handed out.

At the second visit (day 15), diaries were reviewed. Patients who had at least 2 days with mild to moderate pain during the second week of run-in and who fulfilled all inclusion criteria and who did not violate any of the exclusion criteria were 1:1 randomized to receive either B. bifidum MIMBb75 or placebo. The treatment was allocated according to a computer-generated blocked randomisation list with a block size of 4. The block size was not disclosed to the investigators. During the intervention period, patients received either one capsule comprising probiotic formulation daily for 4 weeks or an identical appearing placebo. The allocation was blinded to both patients and site staff.

At the end of the treatment phase (visit 3, day 43), investigators collected unused study product and empty sachets in order to confirm compliance. Diaries were collected and reviewed.

After the nutritional supplement-free wash-out phase (visit 4, day 57), a complete physical examination was performed and a blood sample was taken. Bisacodyl and loperamide were allowed as rescue medication. Other probiotics and medications that could influence the efficacy of the study product were not allowed.

3.4 Probiotic Preparation

Nutritional supplement was prepared under good manufacturing process (GMP) conditions. B. bifidum MIMBb75 was grown in a protein-rich liquid growth medium, harvested through centrifugation, stabilized, freeze-dried, milled and sieved. The dry powder bacteria were mixed with a pharmaceutically acceptable compound and filled into capsules of $1\times10^9$ cfu. Placebo capsules appeared identical and contained maltodextrin.

3.5 Endpoint Definitions

The prospectively defined primary efficacy variable was the subject's global assessment of IBS symptoms using a 7-point Likert scale. Patients were asked to answer the daily question "If you consider your IBS symptoms (e.g. abdominal pain/discomfort, distension/bloating, digestive disorder, urgency, bowel habit) in general, how have you been affected by these symptoms during the last 24 hours?" Possible answers ranged from 0 (not at all), 1 (very mild), 2 (mild), 3 (moderate), 4 (strong), 5 (very strong) to 6 (intolerable).

Secondary efficacy variables included the individual symptoms of IBS alone, such as "abdominal pain/discomfort", "distension/bloating", "digestive disorder" and "urgency", recorded on the same 7-point Likert scale. The individual symptom scores were additionally combined into a composite symptom score as the arithmetic mean of three individual symptom scores. Furthermore, the reduced and/or increased number of bowel movements, feeling of incomplete bowel evacuation and intake of other medication were reported daily in the diary.

At the end of treatment and again at the end of the study, physicians questioned the patients regarding the global assessment of efficacy and tolerability. Efficacy was assessed by the following question: "Please consider how you felt during the 4 week treatment regarding your overall well-being, and symptoms of abdominal discomfort/pain and altered bowel habit. Compared to the way you usually felt before taking the study medication, how would you rate your relief of symptoms during the last 4 weeks?" Possible answers were: "completely relieved (1), considerably relieved (2), somewhat relieved (3), unchanged (4) or worse (5)". Both "completely relieved" and "considerably relieved" were defined as "adequate relief". Health related quality of life was assessed by the use of the SF-12 questionnaire prior to treatment and at the end of the treatment.

Adverse events were recorded throughout the study and the global assessment of tolerability has been questioned at physician visit 3 and 4. Laboratory values and vital signs were examined at the screening visit and at the end of study.

3.6 Statistical Methods 3.6.1 Sample Size Estimation

A reduction of the subject's global assessment (SGA) of at least 20% on the 7-point Likert scale was considered a relevant treatment effect. Based on published data (Whorwell, 2006), a difference of 0.6 points in the SGA of IBS symptoms between *B. bifidum* MIMBb75 and placebo on the 7-point Likert scale was anticipated (e.g. 3.0 in the placebo group and 2.4 in the *Bifidobacteria* group). Standard deviation was estimated with 1.0 using the same data. With these assumptions, a Wilcoxon-Mann-Whitney test with a two-sided significance level of $\alpha=0.05$ and a power of $1-\beta=0.8$, a sample size of 47 patients per group was required. With an estimated drop-out rate of 15-20% after randomisation, 110 randomised patients were planned and 132 patients were recruited to account for possible withdrawals prior to study start.

3.6.2 Statistical Analysis

The primary objective of this study was to prove a significant reduction of the SGA of general IBS symptoms at the end of treatment in the *Bifidobacteria* group vs. placebo. The SGA was calculated for each subject as arithmetic mean at baseline, during the treatment period and during the wash-out phase. To account for possible differences in the baseline values, the change from baseline calculated as mean score during 4 weeks of treatment minus mean score during the run-in phase (week 1-2) was defined as primary target criterion. The non-parametric Van Elteren test stratified by study centres was used for the comparison of treatment arms. P<0.05 was considered statistically significant.

The primary analysis was based on the intent-to-treat population where all successfully randomised patients were included. Missing post-baseline values were imputed by the baseline value for the primary target criterion and these patients were evaluated as non-responders. An additional per protocol analysis was performed for supportive purposes.

Descriptive analyses of secondary target criteria were based on available data.

Treatment differences were tested by use of the non-parametric Wilcoxon test for continuous variables or by Fishers exact test for binary variables. All p-values are two-sided.

Secondary efficacy variables included response based on a 50% rule of symptom relief during treatment (at least improvement in two out of four weeks within the treatment period and improvement defined as at least one point reduction from baseline). All statistical analyses were performed using SAS version 9.1.3 for windows, SAS Institute Inc., Cary, N.C., USA.

3.7 Results 3.7.1 Subjects

A total of 132 patients were included into the study and 122 patients were successfully randomised to receive either placebo (N=62) or *B. bifidum* MIMBb75 (N=60). All randomized patients were analyzed for intent to treat (ITT) (N=122). One patient with no post randomization visit was excluded from the analysis of adverse events. A total of 103 patients (49 placebo, 54 verum) were analysed as per protocol (FIG. 2).

3.7.2 Baseline Characteristics

In terms of baseline characteristics, there were no significant differences between the groups. 21.5% were classified as diarrhoea-predominant IBS, 19.8% as constipation-predominant IBS and 58.7% as alternators with no significant differences between the *Bifidobacteria* and the placebo group.

Demographics were well balanced between the treatment groups with about 67% female patients and mean weight of 71 kg corresponding to a BMI of 24. Patients were on average 41 years in the placebo group and 37 years in the *Bifidobacteria* group (Table 1).

TABLE 1

Demographic characteristics of the intent to treat (ITT)-population. SD—standard deviation, BMI—Body mass index.

| | Placebo N (%) or mean ± SD | Verum N (%) or mean ± SD |
|---|---|---|
| N = 122 (62 + 60) | | |
| Age | 40.98 ± 12.80 | 36.65 ± 12.42 |
| Female sex | 41 (66.1) | 41 (68.3) |
| Height (cm) | 169.50 ± 8.75 | 170.78 ± 9.47 |
| Weight (kg) | 70.79 ± 15.54 | 70.45 ± 16.02 |
| BMI | 24.60 ± 5.19 | 24.02 ± 4.45 |
| IBS Type (N = 122 (61 + 60)) | | |
| Diarrhoea predominant | 12 (19.4) | 14 (23.3) |
| Constipation predominant | 15 (24.2) | 9 (15.0) |
| Alternating type | 34 (54.8) | 37 (61.7) |

3.7.3 Subject's Global Assessment (SGA) of IBS Symptoms

The primary endpoint was the reduction of the SGA of IBS symptoms on the subject's global assessment diary. *B. bifidum* MIMBb75 significantly improved global IBS symptoms by −0.88 points [95% confidence interval (CI): −1.07; −0.69] (from 2.95 in the run in phase to 2.07 in the treatment phase) compared to only −0.16 points [95% CI: −0.32; 0.00] (from 2.79 in the run in phase to 2.63 in the treatment phase) in the placebo group (p<0.0001) using the 7-point Likert scale. The evaluation of the SGA on a weekly basis showed a significant benefit for patients within the *Bifidobacteria* group for every single week starting the second week of treatment till the end of the study (FIG. 3).

3.7.4 Secondary Endpoints

Secondary endpoints included changes in individual IBS symptoms, such as "pain/discomfort", "distension/bloating", "digestive disorder", "urgency", "reduced and/or increased number of bowel movements" and "feeling of incomplete evacuation", on a 7-point Likert scale. *B. bifidum* MIMBb75 showed significant reduction of pain/discomfort by −0.82 points [95% CI: −1.01; −0.63] vs. −0.18 [95% CI: −0.35; −0.01] in the placebo group (p<0.0001), and distension/bloating by −0.92 points [95% CI: −1.15; −0.69] vs. −0.21 [95% CI: −0.37; −0.05] in the placebo group (p<0.0001) during treatment. The reduction persisted during the wash-out phase. Urgency was significantly reduced by −0.67 points [95% CI: −0.86; −0.48] vs. −0.21 [95% CI: −0.35; −0.07] in the placebo group (p=0.0001) during treatment but not during wash-out. No effects could be detected for frequency of bowel movement and feeling of incomplete bowel evacuation (FIG. 4).

The evaluation of the individual IBS symptoms pain/discomfort and distension/bloating on a weekly basis showed a significant benefit for patients within the *Bifidobacteria* group compared to placebo for every single week beginning the second week of treatment till the end of the study. A significant difference in urgency between *Bifidobacteria* and placebo group was shown between week four and six (FIGS. 5 and 6).

Digestive disorder was measured by the item "bowel movement satisfaction" in the questionnaire at physician site. Bowel movement satisfaction decreased from 3.89 to 2.44 in the *Bifidobacteria* group vs. 3.69 to 6.47 in the placebo group (p=0.0002) after treatment. The reduction persisted during washout phase (2.33 in the *Bifidobacteria* group vs. 3.47 in placebo group, p<0.0001).

3.7.5 Composite Score

A composite score was calculated for the individual IBS symptoms (pain/discomfort, distension/bloating, urgency). During the run in phase, the score was comparable in both groups. The patients within the *Bifidobacteria* group significantly benefited from the consumption of *B. bifidum* MIMBb75 vs. placebo (−0.80 in the *Bifidobacteria* group; −0.20 in the placebo group; p<0.0001). This improvement was also preserved during the wash-out phase (−0.85 in the *Bifidobacteria* group; −0.31 in the placebo group; p<0.0001).

3.7.6 Treatment Responders

Overall responders were defined as patients experiencing an improvement of the average weekly score of at least 1 point on the Likert scale for the primary parameter (SGA of IBS symptoms) in at least two out of the 4 weeks treatment period (50% rule). Abdominal pain responders were defined using the same 50% rule for at least one point average improvement for the assessment of "pain/discomfort". Overall responder rates were 56.7% in the *Bifidobacteria* group and only 21.0% in the placebo group (p=0.0001). The difference between the treatment arms was only a little bit less pronounced when considering only the symptom "pain/discomfort" where responder rates were calculated to be 48.3% in the *Bifidobacteria* and only 24.2% in the placebo group (p=0.008) (FIG. 7).

3.7.7 Global Efficacy at Physician Site

The overall assessment of efficacy was significantly better in the *Bifidobacteria* group compared to placebo. At the end of treatment 43.3% of the patients in the *Bifidobacteria* group achieved adequate relief compared to only 8.1% in the placebo group (p<0.0001). At end of the study adequate relief was reported for 46.7% in the *Bifidobacteria* and 11.3% of the patients in the placebo group (p<0.0001; FIG. 8).

3.7.8 Health Related Quality of Life

The evaluation of the SF-12 sum scores showed a significant gain in quality of life within the *Bifidobacteria* group. Physical health sum improved by 3.99 in the *Bifidobacteria* group and by only 1.08 in the placebo group compared to baseline (p=0.0185). Mental health sum improved by 5.78 in the *Bifidobacteria* group and by only 1.58 in the placebo group compared to baseline (p=0.0083).

3.7.9 Adverse Events

Only 36 adverse events were reported with suspected relationship to the study product, 13 in the placebo and 23 in the treatment group, but no significant differences could be detected in the side effects profile of *B. bifidum* MIMBb75 vs. placebo.

3.7.10 Summary

*B. bifidum* MIMBb75 significantly reduced the subject's global assessment (SGA) of IBS symptoms by −0.88 points [95% CI: −1.07; −0.69] compared to only −0.16 [95% CI: −0.32; 0.00] points in the placebo group (p<0.0001). *B. bifidum* MIMBb75 also significantly improved the individual IBS symptoms pain/discomfort, distension/bloating, digestive disorder and urgency. The evaluation of the SF-12 sum scores showed a significant gain in quality of life within the *Bifidobacteria* group. Furthermore, adequate relief was reported by 46.7% of patients in the *Bifidobacteria* and only by 11.3% of patients in the placebo group (p<0.0001). Overall responder rates were 56.7% in the *Bifidobacteria* group and only 21.0% in the placebo group (p=0.0001). *B. bifidum* MIMb75 was well tolerated and the adverse events were not different from placebo.

3.8 Conclusion

*B. bifidum* MIMBb75 effectively alleviates global IBS as well as improves individual IBS symptoms. Considering the high efficacy of *B. bifidum* MIMBb75 in IBS along with the good side effect profile, *B. bifidum* MIMBb75 is a promising candidate for IBS therapy.

This randomised, double blind, placebo-controlled study indicates that *B. bifidum* MIMBb75 has beneficial effects in the treatment of IBS. In this study, *B. bifidum* MIMBb75 significantly improved global IBS and its related symptoms such as pain/discomfort and bloating compared to placebo. Moreover, *B. bifidum* MIMBb75 also significantly improved quality of life. These benefits persisted within the consumption-free wash-out phase. Overall responder rates were predominantly high with 56.7% in the *Bifidobacteria* group compared to only 21.0% in the placebo group (p=0.0001). At the end of the study adequate relief was reported for 46.7% in the *Bifidobacteria* and only 11.3% of the patients in the placebo group (p<0.0001). Up to date, several studies have examined the effects of *Bifidobacteria* on IBS and its symptoms. However, only a few could show a significant benefit. Additionally, to the inventors' knowledge, no probiotic strain could show to significantly alleviate irritable bowel syndrome and simultaneously improve quality of life. While some studies might have missed to show efficacy due to small sample size and randomisation errors, several different probiotic strains did repeatedly show no significant improvement in IBS. Recently, Brenner et al. (2009) published a systematic review of randomised controlled trials (RCTs) aimed at the evaluation of the efficacy, safety, and tolerability of probiotics in the treatment of IBS. A total of 16 RCTs were included in the analysis. Of those, exclusively one *Bifidobacteria* strain showed efficacy for improvement of IBS symptoms in two appropriately designed studies. These findings can be attributed to the fact, that the efficacy of probiotics is strongly strain specific and that only few strains might be able to show efficacy in IBS.

In conclusion, *B. bifidum* MIMBb75 improves global IBS as well as its IBS symptoms along with a good side effect profile.

Figure 1:
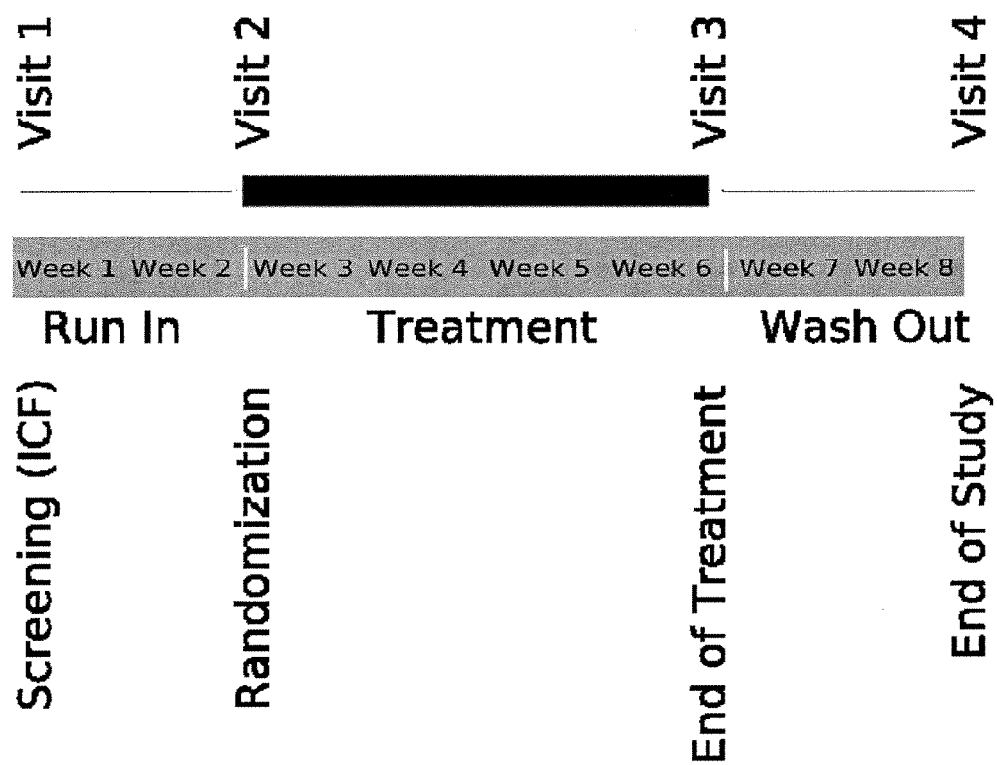
FIG. 1: Study schematic.
Figure 2:
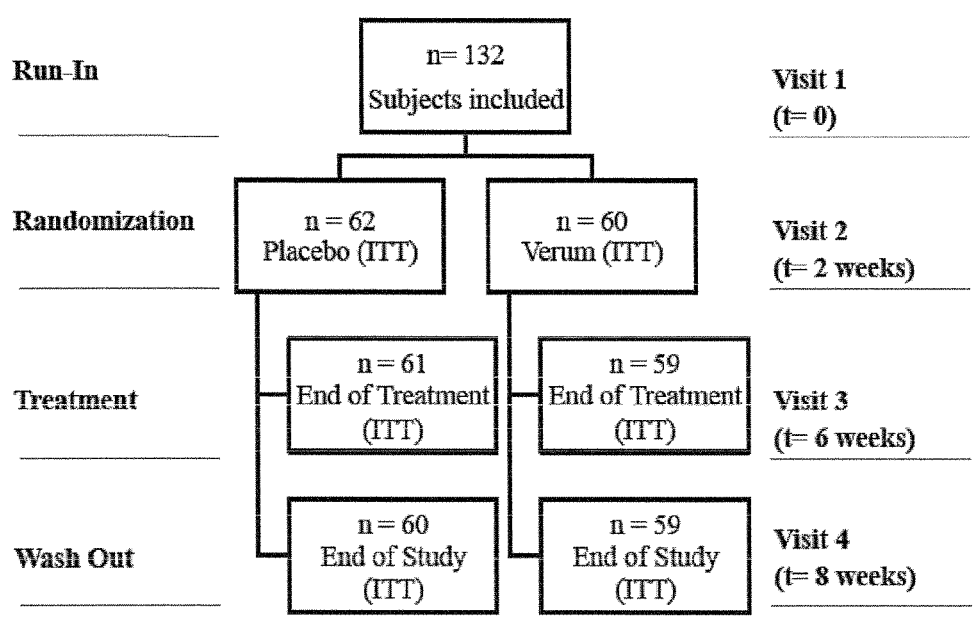
FIG. 2: Diagram of study flow.
Figure 3:
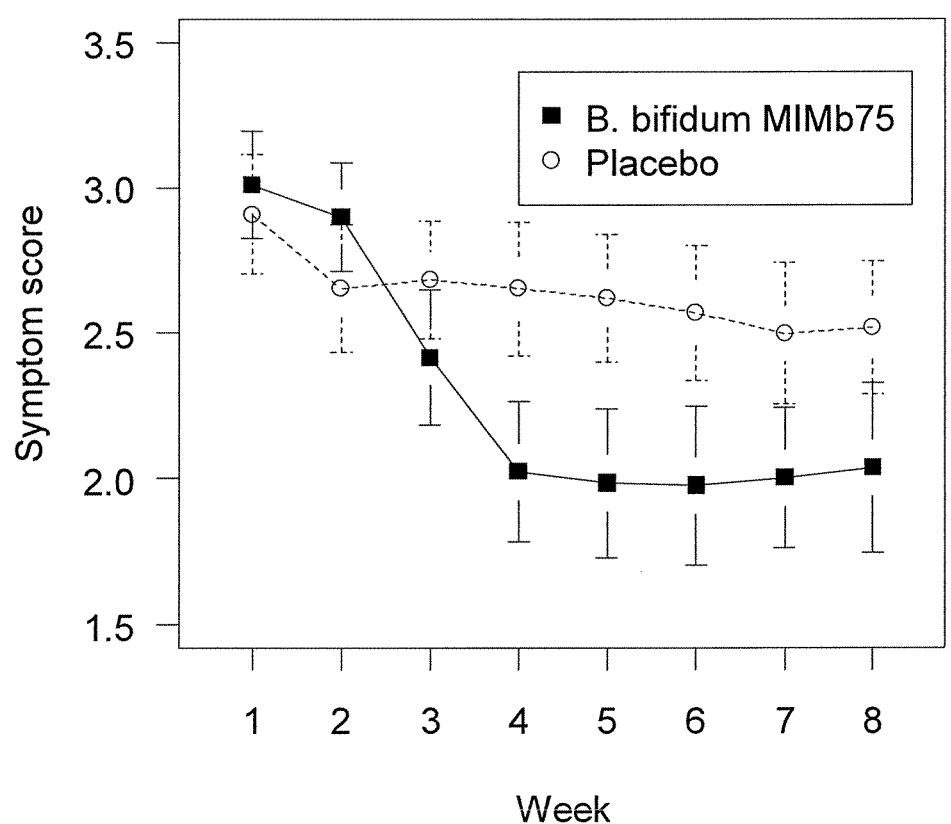
FIG. 3: Comparison of effects of placebo and *B. bifidum* MIMBb75 on global IBS symptoms (by SGA, recorded on a 0-6 scale) on a weekly basis. Significant improvement of global IBS symptoms in the *Bifidobacteria* group vs. placebo.
Figure 4:
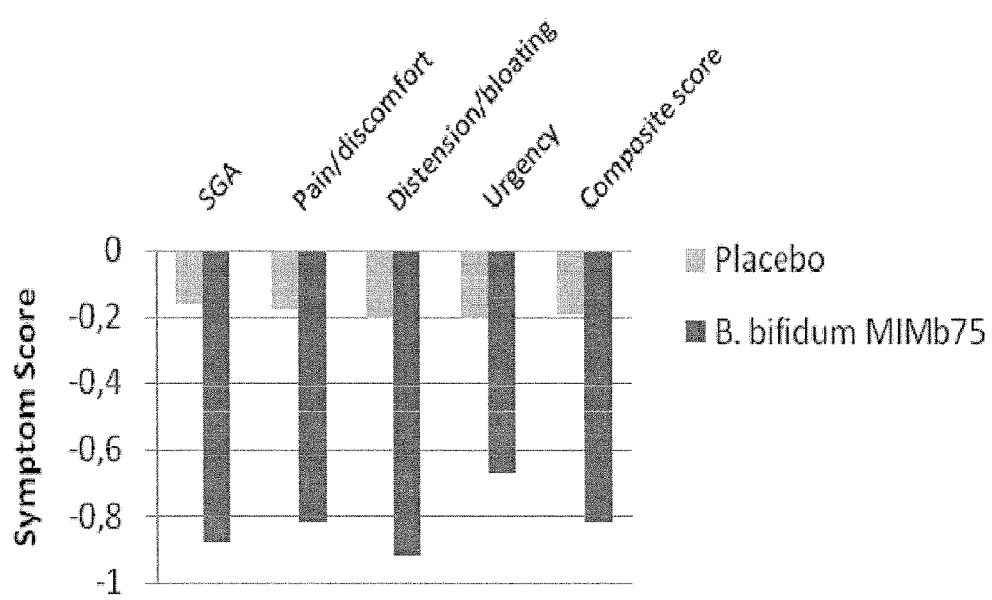
FIG. 4: Comparison of the reduction of IBS symptoms (*B. bifidum* MIMBb75 vs. placebo) on mean score changes from baseline to treatment phase.
Figure 5:
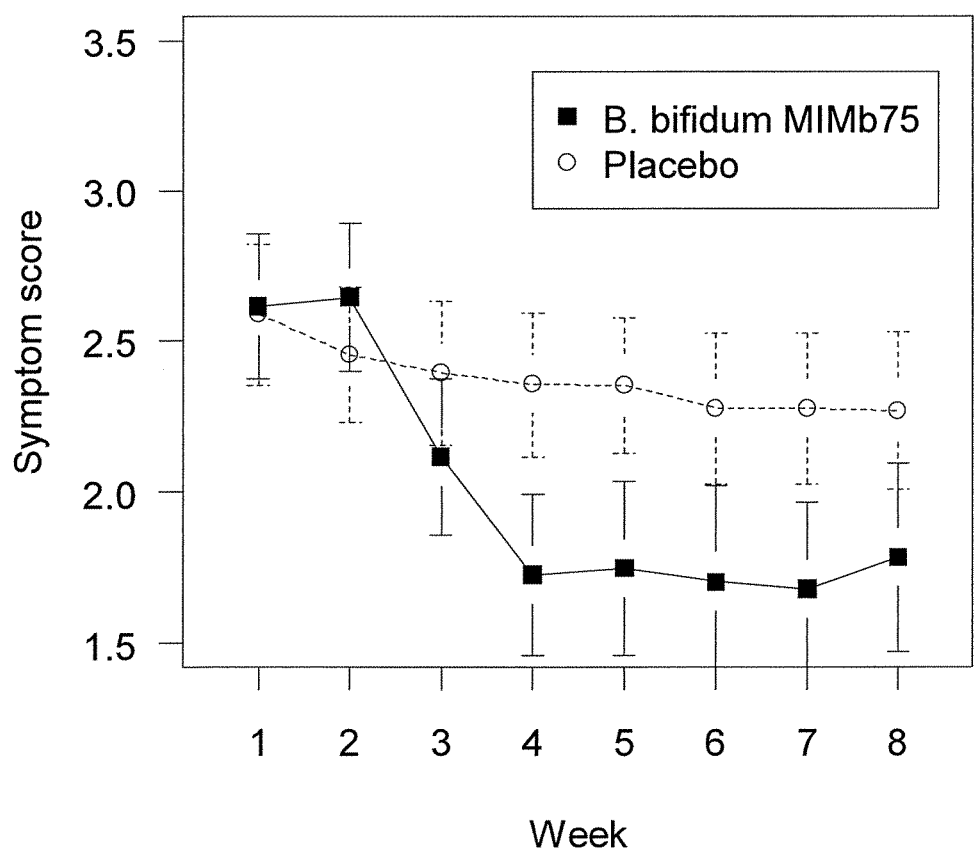
FIG. 5: Comparison of effects of placebo and *B. bifidum* MIMBb75 on pain/discomfort (recorded on a 0-6 Likert scale) on a weekly basis. Significant improvement in the *Bifidobacteria* group vs. placebo group.
Figure 6:
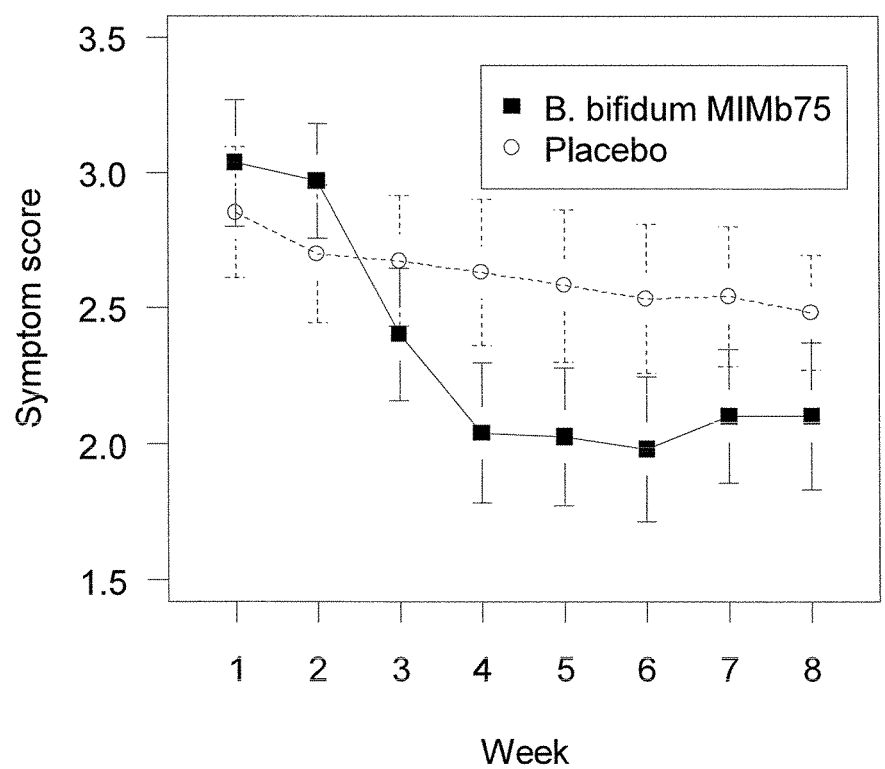
FIG. 6: Comparison of effects of placebo and *B. bifidum* MIMBb75 on distension/bloating (recorded on a 0-6 scale) on a weekly basis. Significant improvement in the *Bifidobacteria* group vs. placebo group.
Figure 7:
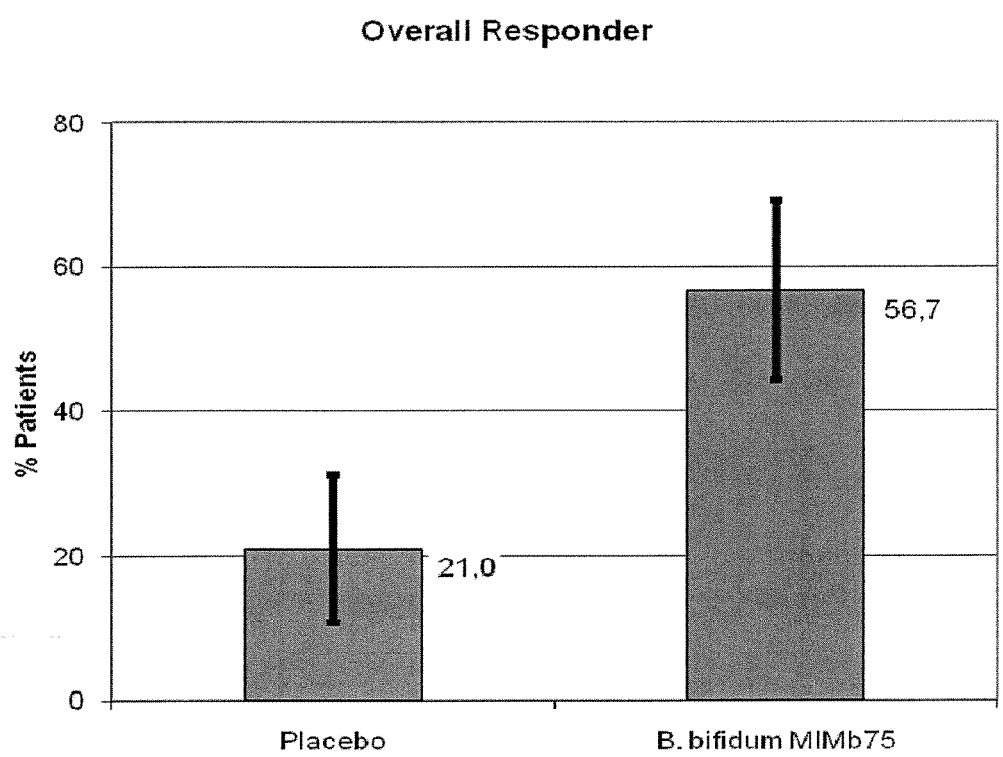
FIG. 7: Overall responders during treatment (ITT).
Figure 8:
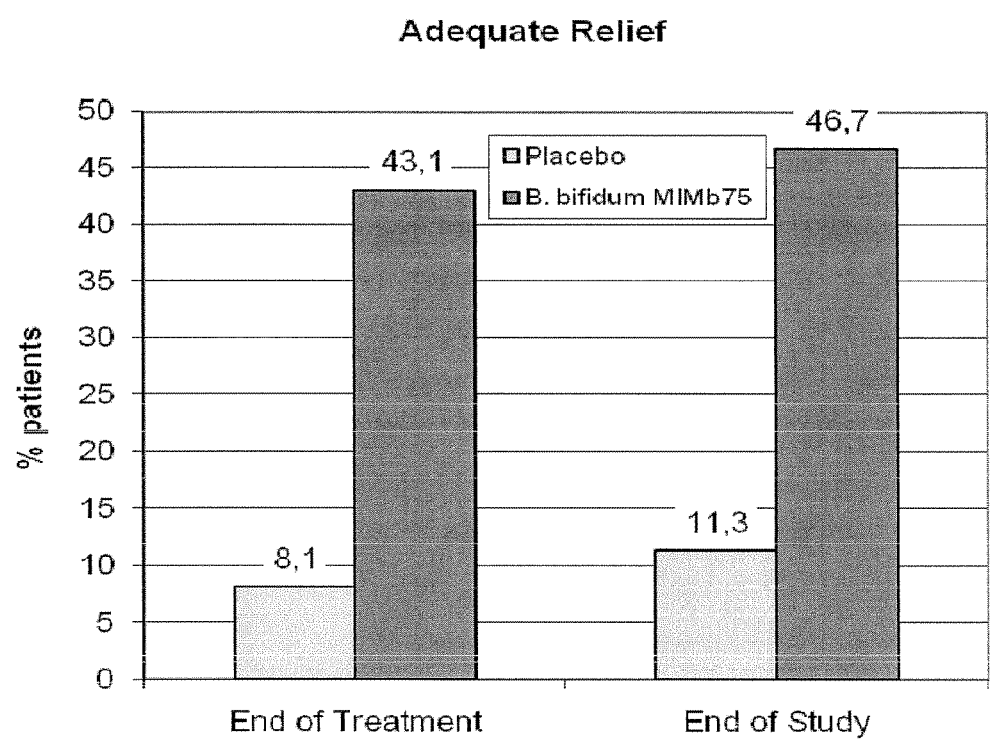
FIG. 8: Adequate relief after treatment (ITT).

The invention claimed is:

1. A method of treatment, comprising administering to a subject in need thereof an effective amount of a probiotic formulation comprising a strain of *Bifidobacterium bifidum* MIMBb75, deposited under deposit No. DSM 24514, wherein the subject is in need of treatment of irritable bowel syndrome.

2. The method of treatment of claim 1, wherein said probiotic formulation further comprises at least inulin and/or a fructooligosaccharide.

3. The method of treatment of claim 1, wherein said probiotic formulation further comprises at least one pharmaceutically acceptable compound, at least one ingestible carrier, at least one adjuvant, at least one bacterial component, at least one drug entity, or at least one biological compound.

4. The method of treatment of claim 3, wherein the ingestible carrier is a capsule, tablet, powder or a food product.

5. The method of treatment of claim 4, wherein the strain is present at more than $10^1$ cfu per capsule or tablet or food product.

6. The method of treatment of claim 5, wherein the strain is present at not less than $10^2$ cfu per capsule or tablet or food product.

7. The method of treatment of claim 5, wherein the strain is present at not less than $10^3$ cfu per capsule or tablet or food product.

8. The method of treatment of claim 5, wherein the strain is present at not less than $10^4$ cfu per capsule or tablet or food product.

9. The method of treatment of claim 5, wherein the strain is present at not less than $10^5$ cfu per capsule or tablet or food product.

10. The method of treatment of claim 5, wherein the strain is present at not less than $10^6$ cfu per capsule or tablet or food product.

11. The method of treatment of claim 4, wherein the daily amount of the strain administered to the subject is not less than $10^1$ cfu.

12. The method of treatment of claim 11, wherein the daily amount of the strain administered to the subject is not less than $10^2$ cfu.

13. The method of treatment of claim 11, wherein the daily amount of the strain administered to the subject is not less than $10^3$ cfu.

14. The method of treatment of claim 11, wherein the daily amount of the strain administered to the subject is not less than $10^4$ cfu.

15. The method of treatment of claim 11, wherein the daily amount of the strain administered to the subject is not less than $10^5$ cfu.

16. The method of treatment of claim 11, wherein the daily amount of the strain administered to the subject is not less than $10^6$ cfu.

17. The method of treatment of claim 4, wherein the food product is a dairy product, acidified milk, yoghurt, frozen yoghurt, milk powder, milk concentrate, cheese spread, dressing or beverage.

18. The method of treatment of claim 3,
wherein said at least one pharmaceutically acceptable compound is selected from the group consisting of vitamins, vitamins of the B group, minerals, calcium minerals, magnesium minerals, trace elements, carbohydrates, lactose, maltodextrin, inulin, dextrose, mannitol, maltose, dextrin, sorbitol and fructose; and/or
wherein the biological compound is selected from the group consisting of a protein, a peptide, protein rich in glutamine/glutamate, peptide rich in glutamine/glutamate and a lipid.

19. A method of treatment, comprising administering to a subject in need thereof an effective amount of a probiotic formulation comprising a strain of *Bifidobacterium bifidum* MIMBb75, deposited under deposit No. DSM 24514, wherein the subject is in need of treatment of abdominal pain, bloating, constipation, digestive disorder, urgency, reduced number of bowel movements, increased number of bowel movements, feeling of incomplete evacuation, or combinations thereof.

20. A method of treatment, comprising administering to a subject in need thereof an effective amount of a probiotic formulation comprising a strain of *Bifidobacterium bifidum* MIMBb75, deposited under deposit No. DSM 24514, wherein the subject is in need of treatment of a disease selected from the group consisting of irritable bowel movement, inflammatory bowel disease, Crohn's disease, ulcerative colitis, pouchitis, post infection colitis, diarrhoeal disease, *Clostridium difficile* associated diarrhoea, and combinations thereof.

* * * * *